United States Patent
Davies et al.

(10) Patent No.: US 9,201,074 B2
(45) Date of Patent: Dec. 1, 2015

(54) ANTI-C-MET ANTIBODIES

(75) Inventors: Julian Davies, La Jolla, CA (US); Ling Liu, Carmel, IN (US); Jirong Lu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/345,456

(22) PCT Filed: Sep. 13, 2012

(86) PCT No.: PCT/US2012/055057
§ 371 (c)(1),
(2), (4) Date: Mar. 18, 2014

(87) PCT Pub. No.: WO2013/043452
PCT Pub. Date: Mar. 28, 2013

(65) Prior Publication Data
US 2014/0349310 A1    Nov. 27, 2014

Related U.S. Application Data

(60) Provisional application No. 61/536,698, filed on Sep. 20, 2011, provisional application No. 61/537,677, filed on Sep. 22, 2011.

(51) Int. Cl.
*A61K 39/395* (2006.01)
*G01N 33/573* (2006.01)
*C07K 16/28* (2006.01)

(52) U.S. Cl.
CPC .......... *G01N 33/573* (2013.01); *C07K 16/2863* (2013.01); *C07K 2317/33* (2013.01); *C07K 2317/565* (2013.01); *C07K 2317/92* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 5,571,509 | A | 11/1996 | Comoglio et al. |
| 6,214,344 | B1 | 4/2001 | Schwall et al. |
| 6,468,529 | B1 | 10/2002 | Schwall et al. |
| 7,494,650 | B2 | 2/2009 | Kim et al. |
| 7,556,804 | B2 | 7/2009 | Prat |
| 7,718,174 | B2 | 5/2010 | Chung et al. |
| 7,892,770 | B2 | 2/2011 | Cao et al. |
| 8,217,148 | B2 | 7/2012 | Davies et al. |
| 2005/0054019 | A1 | 3/2005 | Michaud et al. |

FOREIGN PATENT DOCUMENTS

| WO | WO 92/20792 | A1 | 11/1992 |
|---|---|---|---|
| WO | WO 96/38557 | A1 | 12/1996 |
| WO | WO 03/057155 | A2 | 7/2003 |
| WO | WO 2004/072117 | A2 | 8/2004 |
| WO | WO 2005/016382 | A1 | 2/2005 |
| WO | WO 2005/058965 | A1 | 6/2005 |
| WO | WO 2005/063816 | A2 | 7/2005 |
| WO | WO 2006/015371 | A2 | 2/2006 |
| WO | WO 2006/104911 | A2 | 10/2006 |
| WO | WO 2007/056523 | A2 | 5/2007 |
| WO | WO 2007/059782 | A1 | 5/2007 |
| WO | WO 2007/090807 | A1 | 8/2007 |
| WO | WO 2007/126799 | A2 | 11/2007 |
| WO | WO 2009/007427 | A2 | 1/2009 |
| WO | WO 2009/029591 | A2 | 3/2009 |
| WO | WO 2010/059654 | A1 | 5/2010 |
| WO | WO 2011/110642 | A2 | 9/2011 |
| WO | WO 2011/150454 | A1 | 12/2011 |

OTHER PUBLICATIONS

Tockman et al, Cancer Research vol. 52 p. 2711s (1992).*
Janicke et al Fibrinolysis vol. 4 p. 69 (1990).*
Michaud, et al., Targeting the hepatocyte growth factor receptor c-Met with neutralizing human monoclonal antibodies for the treatment of cancer, (abstract 3027), Proceedings of the American Association for Cancer Research Annual Meeting, vol. 47, pp. 712-713 (Apr. 2006).
Tseng, et al., "Preclinical efficacy of the c-Met inhibitor CE-355621 in a U87 MG mouse xenograft model evaluated by 18F-FDG smallanimal PET," Journal of Nuclear Medicine: Official Publication, Society of Nuclear Medicine, vol. 49, No. 1, pp. 129-134 (Jan. 2008).
Jarvis, "Big Biotechs Take Antibody Approach to Blocking Met Receptors." Chemical & Engineering News, vol. 85, No. 34, pp. 22 (Aug. 20, 2007).
Corvaia, et al., "First Bivalent Fully Antagonistic Anti-c-Met Antibody Targeting the c-Met Receptor: I) in Vitro Mechanism of Action," (poster 835), Proceedings of the American Association for Cancer Research Annual Meeting (Denver, CO)(Apr. 20, 2009).
Goetsch, et al., First Bivalent Fully Antagonistic Anti-c-Met Antibody Targeting the c-Met Receptor: I) in Vivo Activity, poster 2792), Proceedings of the American Association for Cancer Research Annual Meeting (Denver, CO)(Apr. 20, 2009).
Liu, et al. "Targeting the c-Met signaling pathway for cancer therapy." Expert Opin. Investig. Drugs (Review) 17 (7), pp. 997-1011 (2008).
Martens, et al. "A Novel One-Armed Anti-c-MET Antibody Inhibits Glioblastoma Growth In vivo." Clin Cancer Res 2006; 12 (20), pp. 6144-6152 (Oct. 15, 2006).
Van Der Horst, et al., "Discovery of Fully Human Anti-Met Monoclonal Antibodies with Antitumor Activity against Colon Cancer Tumor Models in Vivo, "Neoplasia, vol. 11, No. 4, pp. 355-364 (Apr. 2009).
Cao, et al. "Neutralizing monoclonal antibodies to hepatocyte growth factor/scatter factor (HGF/SF) display antitumor activity in animal models ." Proc Natl Acad Sci U S A.; 98(13), pp. 7443-7448 (Jun. 19, 2001).

(Continued)

*Primary Examiner* — Sheela J Huff
(74) *Attorney, Agent, or Firm* — Robert L. Sharp

(57) ABSTRACT

Provided is a monoclonal antibody, or antigen-binding fragment thereof, that binds to c-Met. Such antibodies, or antigen-binding fragments thereof, are useful in in vivo, ex vivo or in vitro immunochemical and other imaging methods for detecting cell surface c-Met receptor levels for diagnostic, prognostic and predictive purposes, and for optimizing therapeutic regimens in patients harboring tumors in which c-Met is implicated in pathogenesis.

21 Claims, 3 Drawing Sheets

(56) References Cited

OTHER PUBLICATIONS

Dua, et al. "Detection of Hepatocyte Growth Factor (HGF) Ligand-c-MET Receptor Activation in Formalin-Fixed Paraffin Embedded Specimens by a Novel Proximity Assay. " PLoS ONE; 6(1) 2011; e15932. doi:10.1371/journal.pone.0015932.

Goetsch, et al. "Selection criteria for c-Met-targeted therapies : emerging evidence for biomarkers." Biomarkers Med. ; 4(1), pp. 149-170 (2010).

Greenall, et al. "Non-Agonistic Bivalent Antibodies That Promote c-MET Degradation and Inhibit Tumor Growth and Others Specific for Tumor Related c-Met." PLoS ONE; vol. 7(4) (Apr. 2012).

Hay, et al. "Radioimmunoscintography of tumors autocrine for human met and hepatocyte growth factor/scatter factor." Mol Imaging; (1)1, pp. 56-62 (Jan.-Mar. 2002).

Hay, et al. "Nuclear imaging of Met-expressing human and canine cancer xenografts with radiolabeled monoclonal antibodies (MetSeek)." Clin Cancer Res.; 11(19 Pt 2), pp. 7064s-7069s (Oct. 1, 2005).

Jiao, et al. "Construction of human naïve Fab library and characterization of anti-met Fab fragment generated from the library". Mol Biotechnol.; 31(1), pp. 41-54 (Sep. 2005).

Patrick, et al. "Expression and Mutational Analysis of MET in Human Solid Cancers." Genes, Chromosomes & Cancer; 47, pp. 1025-1037 (2008).

Petrelli, et al. "Ab-induced ectodomain shedding mediates hepatocyte growth factor receptor down-regulation and hampers biological activity." Proc Natl Acad Sci; 103(13), pp. 5090-5095 (Mar. 28, 2006).

Prat, et al. "Agonistic monoclonal antibodies against the Met receptor dissect the biological responses to HGF." J Cell Sci; 111 ( Pt 2), pp. 237-247 (Jan. 1998).

Prat, et al., Mol. Cell. Biol.,11, pp. 5954-5962 (1991).

Ginty, et al. "The relative distribution of membranous and cytoplasmic met is a prognostic indicator in stage I and II colon cancer." Clin. Cancer Res. 14(12), pp. 3814-3822 (2008).

Yi, et al. "Expression system for enhanced green fluorescence protein conjugated recombinant antibody fragment." Hybrid Hybridomics; 23(5), pp. 279-286 (Oct. 2004).

Tsarfaty, et al. "The met Proto-Oncogene Receptor and Lumen Formation." Science; vol. 257, pp. 1258-1261 (Aug. 1992).

Pozner-Moulis, et al. "Antibody validation by quantitative analysis of protein expression using expression of Met in breast cancer as a model." Laboratory Investigation; 87, pp. 251-260 (2007).

Ruco, et al., "Expression of Met Protein in Thyroid Tumors." J. of Pathology;180, pp. 266-270 (1996).

Knudsen, et al. "A Novel Multipurpose Monoclonal Antibody for Evaluating Human c-Met Expression in Preclinical and Clinical Settings." Appl Immunohistochem Mol Morphol; (Sep. 23, 2008).

Bottaro, et al. "Identification of the Hepatocyte Growth Factor Receptor as the c-met Proto-Oncogene Product." Science; 251(4995), pp. 802-804 (Feb. 15, 1991).

Gonzatti-Haces, et al. "Characterization of the TPR-MET oncogene p65 and the MET proto-oncogene p140 protein-tyrosine kinases" PNAS; (Jan. 1988).

\* cited by examiner

▽ 2 µg/mL C8-H241 (human IgG4 subtype) capture, 0.5 µg/mL biotinylated-OptD11 detection ◆ no C8-H241 capture, 0.5 µg/mL biotinylated-OptD11 detection ☉ no cMet ECD, 2 µg/mL C8-H241 (human IgG4 subtype) capture, 0.5 µg/mL biotinylated-OptD11 detection ☐ no cMet ECD, no C8-H241 capture, 0.5 µg/mL biotinylated-OptD11 detection

|  | Response (Ru) | Stoichiometry (mAb to cMet-Fc) |
|---|---|---|
| c-Met-ECD-Fc-Flis | 130 | - |
| mAb C8-H241 (human IgG4 subtype) | 69 | 0.91 |
| mAb OptD11 (mouse IgG1 subtype) | 67 | 0.89 |

SEQUENCE LISTING

```
<160> NUMBER OF SEQ ID NOS: 32

<210> SEQ ID NO 1
<211> LENGTH: 12
<212> TYPE: PRT
<213> ORGANISM: Artificial Sequence
<220> FEATURE:
<223> OTHER INFORMATION: synthetic construct

<400> SEQUENCE: 1

Ser Val Ser Ser Ser Ile Ser Ser Thr Asn Leu His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: synthetic construct

<400> SEQUENCE: 2

Gly Thr Ser Asn Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic construct

<400> SEQUENCE: 3

Gln Gln Trp Ser Ser Tyr Pro Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: synthetic construct

<400> SEQUENCE: 4

Gly Tyr Thr Phe Thr Ser Arg Tyr Ile His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: synthetic construct
```

<400> SEQUENCE: 5

Trp Ile Tyr Pro Val Thr Gly Asp Thr Tyr Tyr Asn Glu Lys Phe Lys
1               5                   10                  15
Gly

<210> SEQ ID NO 6
<211> LENGTH: 7
<212> TYPE: PRT
<213> ORGANISM: Artificial Sequence
<220> FEATURE:
<223> OTHER INFORMATION: synthetic construct

<400> SEQUENCE: 6

Gly Gly Gly Met Phe Tyr Tyr
1               5

<210> SEQ ID NO 7
<211> LENGTH: 107
<212> TYPE: PRT
<213> ORGANISM: Artificial Sequence
<220> FEATURE:
<223> OTHER INFORMATION: synthetic construct

<400> SEQUENCE: 7

Glu Thr Thr Val Thr Gln Ser Pro Ala Leu Met Ala Ala Ser Pro Gly
1               5                   10                  15

Glu Lys Val Thr Ile Thr Cys Ser Val Ser Ser Ile Ser Ser Thr
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Gly
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Tyr Thr Phe Gly Gly Gly Thr Lys Leu Glu Ile
            100                 105

<210> SEQ ID NO 8
<211> LENGTH: 321
<212> TYPE: DNA
<213> ORGANISM: Artificial Sequence
<220> FEATURE:
<223> OTHER INFORMATION: synthetic construct

<400> SEQUENCE: 8
gaaacaactg tgacccagtc tccagcactc atggctgcat ctccagggga gaaggtcacc      60
atcacctgca gtgtcagctc aagtataagt tccaccaact acactgtta ccagcagaag     120 tcagagacct cccccaaacc ctggatttat ggcacatcca acctggcttc tggagtccct     180
gttcgcttcg gtggcagtgg atctgggacc tcttattctc tcacaatcag cagcatggag     240
gctgaagatg ctgccactta ttactgtcaa cagtggagta gttacccgta cacgttcgga     300
gggggcacca agctggaaat c                                                321

<210> SEQ ID NO 9
<211> LENGTH: 115
<212> TYPE: PRT
<213> ORGANISM: Artificial Sequence
<220> FEATURE:
<223> OTHER INFORMATION: synthetic construct

<400> SEQUENCE: 9

```
Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Arg
            20                  25                  30

Tyr Ile His Trp Met Lys Gln Arg Pro Gly Gln Gly Leu Glu Trp Ile
        35                  40                  45

Gly Trp Ile Tyr Pro Val Thr Gly Asp Thr Tyr Asn Glu Lys Phe
    50                  55                  60

Lys Gly Lys Ala Thr Leu Thr Ser Asp Lys Ser Ser Thr Ala Tyr
65                  70                  75                  80

Met Gln Ile Ser Ser Leu Thr Ser Asp Asp Ser Ala Val Tyr Phe Cys
                85                  90                  95

Ala Arg Gly Gly Gly Met Phe Tyr Tyr Trp Gly Gln Gly Thr Leu Val
            100                 105                 110

Thr Val Ser
        115
```

<210> SEQ ID NO 10
<211> LENGTH: 345
<212> TYPE: DNA
<213> ORGANISM: Artificial Sequence
<220> FEATURE:
<223> OTHER INFORMATION: synthetic construct

<400> SEQUENCE: 10

```
gaggttcagc tgcagcagtc tggacctgag ctggtgaagc ctggggcttc agtgaggata    60
tcctgcaagg cttctggcta caccttcaca gtcggtata cactggat gaagcagagg      120 cctggacagg gacttgagtg gattggatgg atttatcctg taactggtga tacttactac    180
aatgagaagt tcaagggcaa ggccacactg acttcagaca atcctccag cacagcctac    240 atgcagatca gcagcctgac ctctgacgac tctgcggtct atttctgtgc aaggggcggt    300
ggaatgtttt attactgggg ccaagggact ctggtcactg tctct                    345
```

<210> SEQ ID NO 11
<211> LENGTH: 215
<212> TYPE: PRT
<213> ORGANISM: Artificial Sequence
<220> FEATURE:
<223> OTHER INFORMATION: synthetic construct

<400> SEQUENCE: 11

```
Glu Thr Thr Val Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Thr
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Gly
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95
```

Tyr Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
        130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
        210                 215

<210> SEQ ID NO 12
<211> LENGTH: 645
<212> TYPE: DNA
<213> ORGANISM: Artificial Sequence
<220> FEATURE:
<223> OTHER INFORMATION: synthetic construct

<400> SEQUENCE: 12
gaaacaactg tgacccagtc tccagcactc atggctgcat ctccagggga gaaggtcacc      60
atcacctgca gtgtcagctc aagtataagt tccaccaact acactgtta ccagcagaag     120 tcagagacct cccccaaacc ctggatttat ggcacatcca acctggcttc tggagtccct     180
gttcgcttcg gtggcagtgg atctgggacc tcttattctc tcacaatcag cagcatggag     240
gctgaagatg ctgccactta ttactgtcaa cagtggagta gttacccgta cacgttcgga     300
gggggcacca agctggaaat caaacgggct gatgcggcgc ccactgtatc catcttccca     360
ccatccagtg agcagttaac atctggaggt gcctcagtcg tgtgcttctt gaacaacttc     420
taccccaaag acatcaatgt caagtggaag attgatggca gtgaacgaca aaatggcgtc     480
ctgaacagtt ggactgatca ggacagcaaa gacagcacct acagcatgag cagcaccctc     540
acgttgacca aggacgagta tgaacgacat aacagctata cctgtgaggc cactcacaag     600
acatcaactt cacccattgt caagagcttc aacaggaatg agtgt                    645

<210> SEQ ID NO 13
<211> LENGTH: 440
<212> TYPE: PRT
<213> ORGANISM: Artificial Sequence
<220> FEATURE:
<223> OTHER INFORMATION: synthetic construct

<400> SEQUENCE: 13

Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Arg
            20                  25                  30

Tyr Ile His Trp Met Lys Gln Arg Pro Gly Gln Gly Leu Glu Trp Ile
        35                  40                  45

Gly Trp Ile Tyr Pro Val Thr Gly Asp Thr Tyr Tyr Asn Glu Lys Phe
    50                  55                  60

```
Lys Gly Lys Ala Thr Leu Thr Ser Asp Lys Ser Ser Thr Ala Tyr
 65                  70                  75                  80

Met Gln Ile Ser Ser Leu Thr Ser Asp Asp Ser Ala Val Tyr Phe Cys
                 85                  90                  95

Ala Arg Gly Gly Gly Met Phe Tyr Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Val Thr Val Pro Ser Ser Thr Trp Pro
                180                 185                 190

Ser Glu Thr Val Thr Cys Asn Val Ala His Pro Ala Ser Ser Thr Lys
                195                 200                 205

Val Asp Lys Lys Ile Val Pro Arg Asp Cys Gly Cys Lys Pro Cys Ile
210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
                260                 265                 270

Asp Asp Val Glu Val His Thr Ala Gln Thr Gln Pro Arg Glu Glu Gln
                275                 280                 285

Phe Asn Ser Thr Phe Arg Ser Val Ser Glu Leu Pro Ile Met His Gln
                290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
                340                 345                 350

Lys Asp Lys Val Ser Leu Thr Cys Met Ile Thr Asp Phe Phe Pro Glu
                355                 360                 365

Asp Ile Thr Val Glu Trp Gln Trp Asn Gly Pro Ala Glu Asn Tyr
370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His Thr Glu Lys
                420                 425                 430

Ser Leu Ser His Ser Pro Gly Lys
        435                 440

<210> SEQ ID NO 14
<211> LENGTH: 1320
<212> TYPE: DNA
<213> ORGANISM: Artificial Sequence
<220> FEATURE:
<223> OTHER INFORMATION: synthetic construct
```

<400> SEQUENCE: 14

```
gaggttcagc tgcagcagtc tggacctgag ctggtgaagc ctggggcttc agtgaggata      60
tcctgcaagg cttctggcta caccttcaca agtcggtata cactggat gaagcagagg      120
cctggacagg gacttgagtg gattggatgg atttatcctg taactggtga tacttactac      180
aatgagaagt tcaagggcaa ggccacactg acttcagaca atcctccag cacagcctac      240
atgcagatca gcagcctgac ctctgacgac tctgcggtct atttctgtgc aaggggcggt      300
ggaatgtttt attactgggg ccaagggact ctggtcactg tctctgcagc caaaacgaca      360
cccccatctg tctatccgct agcccctgga tctgccgccc agaccaacag catggtgacc      420
ctgggctgtc tggtgaaggg ctacttccct gagcctgtga cagtgacctg aacagcggc      480
tctctgtcta gcggcgtgca cattccct gccgtgctgc agagcgacct gtacaccctg      540
agcagcagcg tgaccgtgcc tagcagcaca tggcctagcg agaccgtgac atgcaacgtg      600
gcccacccctg cctcttctac caaggtggac aagaagatcg tgcccagaga ctgcggctgc      660
aagccttgca tctgcaccgt gcctgagtg agcagcgtgt tcatcttccc acccaagccc      720
aaggacgtgc tcaccatcac cctcaccccc aaggtcacgt gtgttgtggt agacatcagc      780
aaggatgatc ccgaggtcca gttcagctgg tttgtagatg atgtggaggt gcacacagct      840
cagacgcaac cccgggagga gcagttcaac agcactttcc gctcagtcag tgaacttccc      900
atcatgcacc aggactggct caatggcaag gagttcaaat gcagggtcaa cagtgcagct      960
ttccctgccc ccatcgagaa aaccatctcc aaaaccaaag gcagaccgaa ggctccacag     1020
gtgtacacca ttccacctcc caaggagcag atggccaagg ataaagtcag tctgacctgc     1080
atgataacag acttcttccc tgaagacatt actgtggagt ggcagtggaa tgggcagcca     1140
gcggagaact acaagaacac tcagcccatc atggacacag atggctctta cttcgtctac     1200
agcaagctca atgtgcagaa gagcaactgg gaggcaggaa atactttcac ctgctctgtg     1260
ttacatgagg gcctgcacaa ccaccatact gagaagagcc tctcccactc tcctggtaaa     1320
```

<210> SEQ ID NO 15
<211> LENGTH: 24
<212> TYPE: PRT
<213> ORGANISM: Homo sapiens

<400> SEQUENCE: 15

```
Tyr Lys Thr Gly Pro Val Leu Glu His Pro Asp Cys Phe Pro Cys Gln
 1               5                  10                  15
Asp Cys Ser Ser Lys Ala Asn Leu
             20
```

<210> SEQ ID NO 16
<211> LENGTH: 11
<212> TYPE: PRT
<213> ORGANISM: Homo sapiens

<400> SEQUENCE: 16

```
Cys Phe Pro Cys Gln Asp Cys Ser Ser Lys Ala
 1               5                  10
```

<210> SEQ ID NO 17
<211> LENGTH: 1192
<212> TYPE: PRT
<213> ORGANISM: Artificial Sequence
<220> FEATURE:
<223> OTHER INFORMATION: synthetic construct

```
<400> SEQUENCE: 17

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
    275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
    355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415
```

```
Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
            805                 810                 815

Thr Lys Ala Phe Phe Met Leu Asp Gly Ile Leu Ser Lys Tyr Phe Asp
            820                 825                 830
```

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Leu Glu Val Leu Phe Gln Gly Pro Asp Ile Glu Pro
            930                 935                 940

Lys Ser Cys Asp Lys Thr His Thr Cys Pro Pro Cys Pro Ala Pro Glu
945                 950                 955                 960

Leu Leu Gly Gly Pro Ser Val Phe Leu Phe Pro Pro Lys Pro Lys Asp
                965                 970                 975

Thr Leu Met Ile Ser Arg Thr Pro Glu Val Thr Cys Val Val Val Asp
            980                 985                 990

Val Ser His Glu Asp Pro Glu Val Lys Phe Asn Trp Tyr Val Asp Gly
            995                 1000                1005

Val Glu Val His Asn Ala Lys Thr Lys Pro Arg Glu Glu Gln Tyr
    1010                1015                1020

Asn Ser Thr Tyr Arg Val Val Ser Val Leu Thr Val Leu His Gln
    1025                1030                1035

Asp Trp Leu Asn Gly Lys Glu Tyr Lys Cys Lys Val Ser Asn Lys
    1040                1045                1050

Ala Leu Pro Ala Pro Ile Glu Lys Thr Ile Ser Lys Ala Lys Gly
    1055                1060                1065

Gln Pro Arg Glu Pro Gln Glu Tyr Thr Leu Pro Pro Ser Arg Glu
    1070                1075                1080

Glu Met Thr Lys Asn Gln Val Ser Leu Thr Cys Leu Val Lys Gly
    1085                1090                1095

Phe Tyr Pro Ser Asp Ile Ala Val Glu Trp Glu Ser Asn Gly Gln
    1100                1105                1110

Pro Glu Asn Asn Tyr Lys Thr Thr Pro Pro Val Leu Asp Ser Asp
    1115                1120                1125

Gly Ser Phe Phe Leu Tyr Ser Lys Leu Thr Val Asp Lys Ser Arg
    1130                1135                1140

Trp Gln Gln Gly Asn Val Phe Ser Cys Ser Val Met His Glu Ala
    1145                1150                1155

Leu His Asn His Tyr Thr Gln Lys Ser Leu Ser Leu Ser Pro Gly
    1160                1165                1170

Lys Arg Ile Asp Tyr Lys Asp Asp Asp Lys His Val His His
    1175                1180                1185

His His His His
    1190

<210> SEQ ID NO 18
<211> LENGTH: 1192
<212> TYPE: PRT
<213> ORGANISM: Artificial Sequence
<220> FEATURE:
<223> OTHER INFORMATION: synthetic construct

```
<400> SEQUENCE: 18

Met Lys Ala Pro Ala Val Leu Val Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Ala Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Asn Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro His
            195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Ile His Ala Phe Glu Ser Asn
                245                 250                 255

Asn Phe Ile Tyr Phe Leu Thr Val Gln Arg Glu Thr Leu Asn Ala Gln
            260                 265                 270

Thr Phe His Thr Arg Ile Ile Arg Phe Cys Ser Leu Asn Ser Gly Leu
            275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415
```

```
Arg Ala Glu Phe Thr Thr Ala Leu Gln Arg Val Asp Leu Phe Met Gly
                420                 425                 430

Gln Phe Ser Glu Val Leu Leu Thr Ser Ile Ser Thr Phe Val Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Pro Leu
                485                 490                 495

Asn Gln Asn Gly Tyr Thr Leu Val Val Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
    530                 535                 540

Cys Val Arg Ser Glu Glu Cys Pro Ser Gly Thr Trp Thr Gln Gln Ile
545                 550                 555                 560

Cys Leu Pro Ala Ile Tyr Lys Val Phe Pro Thr Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Ile Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu His
            755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830
```

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Leu Glu Val Leu Phe Gln Gly Pro Asp Ile Glu Pro
930                 935                 940

Lys Ser Cys Asp Lys Thr His Thr Cys Pro Pro Cys Pro Ala Pro Glu
945                 950                 955                 960

Leu Leu Gly Gly Pro Ser Val Phe Leu Phe Pro Pro Lys Pro Lys Asp
                965                 970                 975

Thr Leu Met Ile Ser Arg Thr Pro Glu Val Thr Cys Val Val Val Asp
            980                 985                 990

Val Ser His Glu Asp Pro Glu Val Lys Phe Asn Trp Tyr Val Asp Gly
            995                 1000                1005

Val Glu Val His Asn Ala Lys Thr Lys Pro Arg Glu Glu Gln Tyr
    1010                1015                1020

Asn Ser Thr Tyr Arg Val Val Ser Val Leu Thr Val Leu His Gln
    1025                1030                1035

Asp Trp Leu Asn Gly Lys Glu Tyr Lys Cys Lys Val Ser Asn Lys
    1040                1045                1050

Ala Leu Pro Ala Pro Ile Glu Lys Thr Ile Ser Lys Ala Lys Gly
    1055                1060                1065

Gln Pro Arg Glu Pro Gln Glu Tyr Thr Leu Pro Pro Ser Arg Glu
    1070                1075                1080

Glu Met Thr Lys Asn Gln Val Ser Leu Thr Cys Leu Val Lys Gly
    1085                1090                1095

Phe Tyr Pro Ser Asp Ile Ala Val Glu Trp Glu Ser Asn Gly Gln
    1100                1105                1110

Pro Glu Asn Asn Tyr Lys Thr Thr Pro Pro Val Leu Asp Ser Asp
    1115                1120                1125

Gly Ser Phe Phe Leu Tyr Ser Lys Leu Thr Val Asp Lys Ser Arg
    1130                1135                1140

Trp Gln Gln Gly Asn Val Phe Ser Cys Ser Val Met His Glu Ala
    1145                1150                1155

Leu His Asn His Tyr Thr Gln Lys Ser Leu Ser Leu Ser Pro Gly
    1160                1165                1170

Lys Arg Ile Asp Tyr Lys Asp Asp Asp Lys His Val His His
    1175                1180                1185

His His His His
    1190

<210> SEQ ID NO 19
<211> LENGTH: 932
<212> TYPE: PRT
<213> ORGANISM: Homo sapiens -continued

<400> SEQUENCE: 19

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415
```

```
Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
        530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
        660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830
```

```
Leu Ile Tyr Val His Asn Pro Val Phe Lys Pro Phe Glu Lys Pro Val
            835                 840                 845
Met Ile Ser Met Gly Asn Glu Asn Val Leu Glu Ile Lys Gly Asn Asp
850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
            900                 905                 910
Gln Ala Ile Ser Ser Thr Val Leu Gly Lys Val Ile Val Gln Pro Asp
            915                 920                 925
Gln Asn Phe Thr
        930

<210> SEQ ID NO 20
<211> LENGTH: 283
<212> TYPE: PRT
<213> ORGANISM: Homo sapiens

<400> SEQUENCE: 20

Glu Cys Lys Glu Ala Leu Ala Lys Ser Glu Met Asn Val Asn Met Lys
1               5                   10                  15
Tyr Gln Leu Pro Asn Phe Thr Ala Glu Thr Pro Ile Gln Asn Val Ile
            20                  25                  30
Leu His Glu His His Ile Phe Leu Gly Ala Thr Asn Tyr Ile Tyr Val
        35                  40                  45
Leu Asn Glu Glu Asp Leu Gln Lys Val Ala Glu Tyr Lys Thr Gly Pro
    50                  55                  60
Val Leu Glu His Pro Asp Cys Phe Pro Cys Gln Asp Cys Ser Ser Lys
65                  70                  75                  80
Ala Asn Leu Ser Gly Gly Val Trp Lys Asp Asn Ile Asn Met Ala Leu
                85                  90                  95
Val Val Asp Thr Tyr Tyr Asp Asp Gln Leu Ile Ser Cys Gly Ser Val
            100                 105                 110
Asn Arg Gly Thr Cys Gln Arg His Val Phe Pro His Asn His Thr Ala
        115                 120                 125
Asp Ile Gln Ser Glu Val His Cys Ile Phe Ser Pro Gln Ile Glu Glu
    130                 135                 140
Pro Ser Gln Cys Pro Asp Cys Val Val Ser Ala Leu Gly Ala Lys Val
145                 150                 155                 160
Leu Ser Ser Val Lys Asp Arg Phe Ile Asn Phe Phe Val Gly Asn Thr
                165                 170                 175
Ile Asn Ser Ser Tyr Phe Pro Asp His Pro Leu His Ser Ile Ser Val
            180                 185                 190
Arg Arg Leu Lys Glu Thr Lys Asp Gly Phe Met Phe Leu Thr Asp Gln
        195                 200                 205
Ser Tyr Ile Asp Val Leu Pro Glu Phe Arg Asp Ser Tyr Pro Ile Lys
    210                 215                 220
Tyr Val His Ala Phe Glu Ser Asn Asn Phe Ile Tyr Phe Leu Thr Val
225                 230                 235                 240
Gln Arg Glu Thr Leu Asp Ala Gln Thr Phe His Thr Arg Ile Ile Arg
                245                 250                 255
```

```
Phe Cys Ser Ile Asn Ser Gly Leu His Ser Tyr Met Glu Met Pro Leu
                260                 265                 270

Glu Cys Ile Leu Thr Glu Lys Arg Lys Lys Arg
        275                 280

<210> SEQ ID NO 21
<211> LENGTH: 212
<212> TYPE: PRT
<213> ORGANISM: Homo sapiens

<400> SEQUENCE: 21

Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
            20                  25                  30

Asp Ile Leu Phe Gly Val Phe Ala Gln Ser Lys Pro Asp Ser Ala Glu
        35                  40                  45

Pro Met Asp Arg Ser Ala Met Cys Ala Phe Pro Ile Lys Tyr Val Asn
    50                  55                  60

Asp Phe Phe Asn Lys Ile Val Asn Lys Asn Asn Val Arg Cys Leu Gln
65                  70                  75                  80

His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Thr Glu
            100                 105                 110

Phe Thr Thr Ala Leu Gln Arg Val Asp Leu Phe Met Gly Gln Phe Ser
        115                 120                 125

Glu Val Leu Leu Thr Ser Ile Ser Thr Phe Ile Lys Gly Asp Leu Thr
130                 135                 140

Ile Ala Asn Leu Gly Thr Ser Glu Gly Arg Phe Met Gln Val Val Val
145                 150                 155                 160

Ser Arg Ser Gly Pro Ser Thr Pro His Val Asn Phe Leu Leu Asp Ser
                165                 170                 175

His Pro Val Ser Pro Glu Val Ile Val Glu His Thr Leu Asn Gln Asn
            180                 185                 190

Gly Tyr Thr Leu Val Ile Thr Gly Lys Lys Ile Thr Lys Ile Pro Leu
        195                 200                 205

Asn Gly Leu Gly
    210

<210> SEQ ID NO 22
<211> LENGTH: 12
<212> TYPE: PRT
<213> ORGANISM: Artificial Sequence
<220> FEATURE:
<223> OTHER INFORMATION: synthetic construct

<400> SEQUENCE: 22

Ser Val Ser Ser Val Ser Ser Ile Tyr Leu His
1               5                   10

<210> SEQ ID NO 23
<211> LENGTH: 7
<212> TYPE: PRT
<213> ORGANISM: Artificial Sequence
<220> FEATURE:
<223> OTHER INFORMATION: synthetic construct
```

```
<400> SEQUENCE: 23

Ser Thr Ser Asn Leu Ala Ser
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic construct

<400> SEQUENCE: 24

Gln Val Tyr Ser Gly Tyr Pro Leu Thr
1               5

<210> SEQ ID NO 25
<211> LENGTH: 10
<212> TYPE: PRT
<213> ORGANISM: Artificial Sequence
<220> FEATURE:
<223> OTHER INFORMATION: synthetic construct

<400> SEQUENCE: 25

Gly Tyr Thr Phe Thr Asp Tyr Tyr Met His
1               5                   10

<210> SEQ ID NO 26
<211> LENGTH: 17
<212> TYPE: PRT
<213> ORGANISM: Artificial Sequence
<220> FEATURE:
<223> OTHER INFORMATION: synthetic construct

<400> SEQUENCE: 26

Arg Val Asn Pro Asn Arg Arg Gly Thr Thr Tyr Asn Gln Lys Phe Glu
1               5                   10                  15

Gly

<210> SEQ ID NO 27
<211> LENGTH: 6
<212> TYPE: PRT
<213> ORGANISM: Artificial Sequence
<220> FEATURE:
<223> OTHER INFORMATION: synthetic construct

<400> SEQUENCE: 27

Ala Asn Trp Leu Asp Tyr
1               5

<210> SEQ ID NO 28
<211> LENGTH: 108
<212> TYPE: PRT
<213> ORGANISM: Artificial Sequence
<220> FEATURE:
<223> OTHER INFORMATION: synthetic construct

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Ser Val Ser Ser Ile
                20                  25                  30

Tyr Leu His Trp Tyr Gln Gln Lys Pro Gly Lys Ala Pro Lys Leu Leu
            35                  40                  45
```

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys
                100                 105

<210> SEQ ID NO 29
<211> LENGTH: 114
<212> TYPE: PRT
<213> ORGANISM: Artificial Sequence
<220> FEATURE:
<223> OTHER INFORMATION: synthetic construct

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Arg Val Asn Pro Asn Arg Arg Gly Thr Thr Tyr Asn Gln Lys Phe
        50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
                100                 105                 110

Val Ser

<210> SEQ ID NO 30
<211> LENGTH: 215
<212> TYPE: PRT
<213> ORGANISM: Artificial Sequence
<220> FEATURE:
<223> OTHER INFORMATION: synthetic construct

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Ser Val Ser Ser Ile
                20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

```
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 31
<211> LENGTH: 440
<212> TYPE: PRT
<213> ORGANISM: Artificial Sequence
<220> FEATURE:
<223> OTHER INFORMATION: synthetic construct

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Thr Thr Tyr Asn Gln Lys Phe
50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270
```

```
Val Asp Gly Met Glu Val His Asn Ala Lys Thr Lys Pro Arg Glu Glu
            275                 280                 285

Gln Phe Asn Ser Thr Phe Arg Val Val Ser Val Leu Thr Val Val His
        290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly
        435                 440

<210> SEQ ID NO 32
<211> LENGTH: 441
<212> TYPE: PRT
<213> ORGANISM: Artificial Sequence
<220> FEATURE:
<223> OTHER INFORMATION: synthetic construct

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Arg Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

-continued

```
Thr Lys Thr Tyr Thr Cys Asn Val Asp His Lys Pro Ser Asn Thr Lys
    195                 200             205

Val Asp Lys Arg Val Glu Ser Lys Tyr Gly Pro Pro Cys Pro Pro Cys
    210                 215             220

Pro Ala Pro Glu Ala Ala Gly Gly Pro Ser Val Phe Leu Phe Pro Pro
225             230             235             240

Lys Pro Lys Asp Thr Leu Met Ile Ser Arg Thr Pro Glu Val Thr Cys
            245             250             255

Val Val Val Asp Val Ser Gln Glu Asp Pro Glu Val Gln Phe Asn Trp
            260             265             270

Tyr Val Asp Gly Val Glu Val His Asn Ala Lys Thr Lys Pro Arg Glu
        275             280             285

Glu Gln Phe Asn Ser Thr Tyr Arg Val Val Ser Val Leu Thr Val Leu
    290             295             300

His Gln Asp Trp Leu Asn Gly Lys Glu Tyr Lys Cys Lys Val Ser Asn
305             310             315             320

Lys Gly Leu Pro Ser Ser Ile Glu Lys Thr Ile Ser Lys Ala Lys Gly
            325             330             335

Gln Pro Arg Glu Pro Gln Val Tyr Thr Leu Pro Pro Ser Gln Glu Glu
            340             345             350

Met Thr Lys Asn Gln Val Ser Leu Thr Cys Leu Val Lys Gly Phe Tyr
    355             360             365

Pro Ser Asp Ile Ala Val Glu Trp Glu Ser Asn Gly Gln Pro Glu Asn
    370             375             380

Asn Tyr Lys Thr Thr Pro Pro Val Leu Asp Ser Asp Gly Ser Phe Phe
385             390             395             400

Leu Tyr Ser Arg Leu Thr Val Asp Lys Ser Arg Trp Gln Glu Gly Asn
            405             410             415

Val Phe Ser Cys Ser Val Met His Glu Ala Leu His Asn His Tyr Thr
            420             425             430

Gln Lys Ser Leu Ser Leu Ser Leu Gly
        435             440
```

ANTI-C-MET ANTIBODIES

This application is a national phase application under 35 U.S.C. §371 for PCT/US2012/055057, filed Sep. 13, 2012, which claims priority to U.S. Provisional Application No. 61/536,698, filed Sep. 20, 2011, and U.S. Provisional Application No. 61/537,677, filed Sep. 22, 2011.

The present invention relates to the field of medicine. More particularly, the invention relates to antibodies that bind c-Met to form a detectable c-Met/anti-c-Met monoclonal antibody complex useful in diagnostic techniques that require labeling, marking, or identifying c-Met such as imaging, prognostic or predictive applications that aid in identifying patients with tumors expressing high levels of c-Met and/or improving their treatment response with anti-c-Met therapeutics.

The protein c-Met is a member of the receptor tyrosine kinase superfamily, and the receptor for hepatocyte growth factor (HGF) also known as scatter factor (SF). The mature c-Met protein is composed of a completely extracellular alpha subunit, a beta subunit comprised of an extracellular ligand binding domain, a single transmembrane domain, and a cytoplasmic tyrosine kinase domain.

Activation of c-Met by HGF has been shown to enhance characteristics that are associated with invasive cell phenotype: proliferation, migration, morphogenesis, survival (including protection from apoptosis), and protease synthesis. The c-Met signaling pathway is one of the most frequently dysregulated pathways in human cancers, and occurs in virtually all types of solid tumors (Knudsen et al. (2008) *Current Opinion in Genetics & Development* 18:87-96). The stimulation, overexpression, or mutation of c-Met is observed in many types of cancers, including colon, breast, ovary, lung, liver, prostate, thyroid, kidney, as well as melanomas and sarcomas. These biochemical and genetic abnormalities of the HGF/c-Met signaling axis are correlated with poor clinical outcomes and drug resistance in cancer patients (Liu, et al., *Expert Opin. Investig. Drugs.* 17(7):997-1011 (2008)).

Due to the role of the c-Met signaling pathway in regulating initial steps of tumor formation and subsequent disease dissemination, c-Met is considered to be an attractive target for cancer therapy with small molecule and antibody antagonists of HGF and/or c-Met in development.

Prat, et al. (*Mol. Cell. Biol.*, 11:5954-5962 (1991)) and PCT International Publication WO 92/20792 disclose several monoclonal antibodies that bind the extracellular domain (ECD) of the β-chain of c-Met, and their use to detect distribution of c-Met in normal and neoplastic human tissues.

PCT International Publication WO 2009/029591 discloses a monoclonal antibody, designated MET4, capable of staining c-Met in formalin fixed and paraffin embedded (FFPE) tumor tissues.

For evaluation of the level of expression of c-Met by tumor cells of a cancer patient and/or determining if the treatment of a patient with one or more therapeutic anti-c-Met agents has resulted in a decreased level of c-Met expression by tumor cells and/or a reduced number of c-Met expressing tumor cells, there is a critical need for c-Met diagnostic antibodies that can specifically bind to membrane localized c-Met particularly when the c-Met is already bound to a therapeutic anti-c-Met agent. Dual binding of a c-Met antibody of the present invention with an anti-c-Met therapeutic agent permits diagnostic assessment of tumor tissue, both before and after treatment of the patient, without compromising the desired diagnostic detection effect.

Accordingly, the invention provides alternative anti-c-Met antibodies that specifically bind to the extracellular domain (ECD) of human c-Met. The anti-c-Met antibodies of the present invention may be useful as diagnostics to aid in identification of cancer patients with tumor cells expressing relatively high levels of c-Met. Furthermore, such anti-c-Met antibodies may be used to monitor and/or optimize a cancer patient's treatment with c-Met targeted therapeutic agents, such as the small molecule antagonists of c-Met described in WO 2010/011538 and U.S. Patent Application Publication No. 2012/0028984 as well as antibody antagonists of c-Met such as those described in WO 2010/059654 and/or U.S. Pat. No. 8,217,148.

One aspect of this invention pertains to a monoclonal antibody, or antigen-binding fragment thereof, that specifically binds to the ECD of human c-Met consisting of the amino acid sequence as in SEQ ID NO: 19, said antibody, or antigen-binding fragment thereof, comprising:

light chain complementarity determining regions LCDR1, LCDR2, and LCDR3 comprising the amino acid sequences SVSSSISSTNLH (SEQ ID NO: 1), GTSNLAS (SEQ ID NO: 2), and QQWSSYPYT (SEQ ID NO: 3), respectively, and heavy chain complementarity determining regions HCDR1, HCDR2, and HCDR3 comprising the amino acid sequences GYTFTSRYIH (SEQ ID NO: 4), WIYPVTGD-TYYNEKFKG (SEQ ID NO: 5), and GGGMFYY (SEQ ID NO: 6), respectively.

Another embodiment of the invention is a monoclonal antibody, or antigen-binding fragment thereof, that specifically binds to the ECD of human c-Met consisting of the amino acid sequence as in SEQ ID NO: 19, said monoclonal antibody comprising:

a light chain variable region (LCVR) comprising the amino acid sequence as in SEQ ID NO: 7, and a heavy chain variable region (HCVR) comprises the amino acid sequence as in SEQ ID NO: 9.

In another embodiment, the invention provides a monoclonal antibody, or antigen-binding fragment thereof, that specifically binds to the ECD of human c-Met consisting of the amino acid sequence as in SEQ ID NO: 19, said monoclonal antibody comprising:

a light chain comprising the amino acid sequence as in SEQ ID NO: 11, and a heavy chain comprising the amino acid sequence as in SEQ ID NO: 13.

In another embodiment, the invention provides a monoclonal antibody, or antigen-binding fragment thereof, that specifically binds to the ECD of human c-Met consisting of the amino acid sequence as in SEQ ID NO: 19, said monoclonal antibody comprising two light chains and two heavy chains, wherein each light chain is the polypeptide of SEQ ID NO: 11, and each heavy chain is the polypeptide of SEQ ID NO: 13.

Another embodiment of the invention provides a diagnostically useful composition comprising one of the foregoing anti-c-Met monoclonal antibodies, or antigen-binding fragments thereof, of the present invention and a diagnostically acceptable carrier, diluent, or excipient. In one such embodiment, the c-Met monoclonal antibody, or antigen-binding fragment thereof, is covalently, non-covalently, or partially covalently and partially non-covalently linked to a detectable moiety.

In another embodiment, the invention encompasses a composition comprising at least one of the foregoing anti-c-Met monoclonal antibodies, or antigen-binding fragments thereof, of the present invention bound to a polypeptide comprising the ECD of human c-Met consisting of the amino acid sequence as in SEQ ID NO: 19. Preferably, an anti-c-Met monoclonal antibody, or antigen-binding fragment thereof, of the present invention is bound to a polypeptide comprising the ECD of human c-Met consisting of the amino acid sequence as in SEQ ID NO: 19 at an epitope within the amino acid sequence as in SEQ ID NO: 15 or 16. More preferably, a composition comprising at least one of the foregoing anti-c-Met monoclonal antibodies, or antigen-binding fragments thereof, of the present invention bound to a polypeptide comprising the ECD of human c-Met consisting of the amino acid sequence as in SEQ ID NO: 19 further comprises a diagnostically acceptable carrier, diluent, or excipient.

In other embodiments, the invention provides a kit, comprising a container comprising a monoclonal antibody, or antigen-binding fragment thereof, that specifically binds to the ECD of human c-Met consisting of the amino acid sequence as in SEQ ID NO: 19, said monoclonal antibody, or antigen-binding fragment thereof, comprising:

light chain complementarity determining regions LCDR1, LCDR2, and LCDR3 comprising the amino acid sequences SVSSSISSTNLH (SEQ ID NO: 1), GTSNLAS (SEQ ID NO: 2), and QQWSSYPYT (SEQ ID NO: 3), respectively, and heavy chain complementarity determining regions HCDR1, HCDR2, and HCDR3 comprising the amino acid sequences GYTFTSRYIH (SEQ ID NO: 4), WIYPVTGD-TYYNEKFKG (SEQ ID NO: 5), and GGGMFYY (SEQ ID NO: 6), respectively. In certain embodiments, the kit may comprise a second container comprising a secondary antibody that binds to the monoclonal antibody, or antigen-binding fragment thereof, and, optionally, instructions for using the monoclonal antibody, or antigen-binding fragment thereof, with or without the secondary antibody, to detect c-Met in vivo, ex vivo or in vitro. In some embodiments, the secondary antibody can be conjugated to an enzyme known to be used in immunoassays. In other embodiments, the kit can further comprise another container comprising a chromogenic substrate of the aforementioned enzyme. Preferably, the methods described herein are for detecting c-Met expression or over-expression are in vitro methods. Likewise, the kits described herein are used to detect c-Met expression or over-expression in vitro, preferably.

In other embodiments, the invention also encompasses a method of detecting c-Met expressed or overexpressed by a mammalian cell comprising: (a) contacting a cell with a detectably labeled monoclonal antibody, or antigen-binding fragment thereof, that specifically binds to the ECD of human c-Met consisting of the amino acid sequence as in SEQ ID NO: 19, said monoclonal antibody, or antigen-binding fragment thereof, comprising:

light chain complementarity determining regions LCDR1, LCDR2, and LCDR3 comprising the amino acid sequences SVSSSISSTNLH (SEQ ID NO: 1), GTSNLAS (SEQ ID NO: 2), and QQWSSYPYT (SEQ ID NO: 3), respectively, and heavy chain complementarity determining regions HCDR1, HCDR2, and HCDR3 comprising the amino acid sequences GYTFTSRYIH (SEQ ID NO: 4), WIYPVTGD-TYYNEKFKG (SEQ ID NO: 5), and GGGMFYY (SEQ ID NO: 6), for a time and under conditions that permit said monoclonal antibody to bind to the ECD of the c-Met expressed by the cell; (b) optionally, removing any non-specifically bound monoclonal antibody or antigen-binding fragment thereof; and (c) detecting and/or quantifying the amount of labeled monoclonal antibody or antigen-binding fragment thereof which is specifically bound to the ECD using any art-known method (for example, cytometric techniques). Preferably, the c-Met is detected in a biological tissue or a bodily fluid obtained from a cancer patient such as in urine, ascites fluid, lymphatic fluid, spinal fluid, bronchial fluid, blood serum or, preferably, blood.

The invention also provides a method of detecting and/or quantifying tumor cells and/or circulating tumor cells expressing or over-expressing c-Met in a mammalian biological tissue or a bodily fluid obtained from a cancer patient such as in urine, ascites fluid, lymphatic fluid, spinal fluid, bronchial fluid, blood serum, or, preferably, blood, comprising: a step of contacting the tissue with a monoclonal antibody, or antigen-binding fragment thereof, that specifically binds to the ECD of human c-Met consisting of the amino acid sequence as in SEQ ID NO: 19, said monoclonal antibody, or antigen-binding fragment thereof, comprising:

light chain complementarity determining regions LCDR1, LCDR2, and LCDR3 comprising the amino acid sequences SVSSSISSTNLH (SEQ ID NO: 1), GTSNLAS (SEQ ID NO: 2), and QQWSSYPYT (SEQ ID NO: 3), respectively, and heavy chain complementarity determining regions HCDR1, HCDR2, and HCDR3 comprising the amino acid sequences GYTFTSRYIH (SEQ ID NO: 4), WIYPVTGD-TYYNEKFKG (SEQ ID NO: 5), and GGGMFYY (SEQ ID NO: 6) under conditions that permit formation of a detectable c-Met/anti-c-Met monoclonal antibody complex; and a next step of detecting and/or quantifying said complex(es). In various embodiments, the contacting can be carried out in vitro. In various embodiments, the contacting can be carried out in vivo. For example, in various embodiments, the anti-c-Met monoclonal antibody, or antigen-binding fragment thereof, can be administered parenterally, by injection or infusion. Additionally, in various embodiments, the anti-c-Met monoclonal antibody, or antigen-binding fragment thereof, is labeled with at least one detectable agent including, but not limited to, the aforementioned labels. Detection can be performed in vitro or in vivo using a method, technology and/or device known in the art to be appropriate for a specific detectable label including, but not limited to, a gamma counter, a scintillation counter, by autoradiography, and/or devices including, for example, a fluorescence measuring device, a bioluminescence measuring device, a magnetic resonance imaging (MRI) device, a magnetic device, a positron emission tomography (PET) device, a computed tomography (CT) device, an ultrasound device, an optical coherence tomography (OCT) device, and/or a single photon emission computed tomography (SPECT) device.

In another embodiment, the invention provides the use of a kit comprising a monoclonal antibody, or antigen-binding fragment thereof, that specifically binds to the ECD of human c-Met consisting of the amino acid sequence as in SEQ ID NO: 19, said monoclonal antibody, or antigen-binding fragment thereof, comprising:

light chain complementarity determining regions LCDR1, LCDR2, and LCDR3 comprising the amino acid sequences SVSSSISSTNLH (SEQ ID NO: 1), GTSNLAS (SEQ ID NO: 2), and QQWSSYPYT (SEQ ID NO: 3), respectively, and heavy chain complementarity determining regions HCDR1, HCDR2, and HCDR3 comprising the amino acid sequences GYTFTSRYIH (SEQ ID NO: 4), WIYPVTGD-TYYNEKFKG (SEQ ID NO: 5), and GGGMFYY (SEQ ID NO: 6), for:

(a) detecting and/or quantifying human c-Met in or on a human cell;
(b) detecting and/or quantifying c-Met expressing or over-expressing tumor cells in a patient;
(c) detecting and/or quantifying c-Met expressing or over-expressing circulating tumor cells in a blood sample of a patient;
(d) detecting and/or quantifying c-Met expressing or over-expressing tumor cells in a bodily fluid from a cancer patient such as in urine, ascites fluid, lymphatic fluid, spinal fluid, bronchial fluid, blood serum or blood;
(e) assessing whether an individual has, or is at risk for developing, cancer of a tissue or organ wherein c-Met is expressed or over-expressed;
(f) identifying a patient having a tumor suitable for treatment with an anti-c-Met therapeutic;
(g) determining response to treatment with anti-c-Met therapeutic antibody or chemotherapeutic agent; and/or
(h) treating cancer.

Preferably, with respect to (a)-(d) above, the detecting or quantifying is carried out in vitro. More preferably, with respect to (a)-(d) above, the detecting and quantifying are are each performed in vitro. Also, with respect to (g) and (h) above, the treatment preferably includes the administration of an anti-c-Met therapeutic antibody such as an anti-c-Met antibody described in, for example, WO 2010/059654 and/or U.S. Pat. No. 8,217,148, and/or an anti-c-Met chemotherapeutic agent such as the compound, or pharmaceutically acceptable salt thereof, disclosed in WO 2010/011538 and U.S. Patent Application Publication No. 2012/0028984. More preferably, with respect to (g) and (h) above, the treatment includes the administration of an anti-c-Met therapeutic antibody, or antigen-binding fragment thereof, that specifically binds to the extracellular domain (ECD) of human c-Met consisting of the amino acid sequence as in SEQ ID NO: 19, the antibody, or fragment thereof, comprising:

light chain complementarity determining regions LCDR1, LCDR2, and LCDR3 comprising the amino acid sequences SEQ ID NO: 22, SEQ ID NO: 23, and SEQ ID NO: 24, respectively, and heavy chain complementarity determining regions HCDR1, HCDR2, and HCDR3 comprising the amino acid sequences SEQ ID NO: 25, SEQ ID NO: 26, and SEQ ID NO: 27, respectively.

Even more preferably, with respect to (g) and (h) above, the treatment includes the administration of an anti-c-Met therapeutic antibody, or antigen-binding fragment thereof, comprising a light chain variable region (LCVR) comprising the amino acid sequence as in SEQ ID NO: 28, and a heavy chain variable region (HCVR) comprises the amino acid sequence as in SEQ ID NO: 29.

Even more preferably, with respect to (g) and (h) above, the treatment includes the administration of an anti-c-Met therapeutic antibody, or antigen-binding fragment thereof, comprising a light chain comprising the amino acid sequence as in SEQ ID NO: 30, and a heavy chain comprising the amino acid sequence as in SEQ ID NO: 31 or 32.

Even more preferably, with respect to (g) and (h) above, the treatment includes the administration of an anti-c-Met therapeutic antibody comprising two light chains and two heavy chains, wherein each of the light chains consist of the amino acid sequence as in SEQ ID NO: 30 and each of the heavy chains consist of the amino acid sequence as in SEQ ID NO: 31 or 32 (an human IgG2 or human IgG4 subtype, respectively, of the anti-c-Met therapeutic antibody referred to as C8-H241 in WO 2010/059654 and/or U.S. Pat. No. 8,217,148) or the chemotherapeutic agents shown below as Structure 1 and Structure 2, or pharmaceutically acceptable salts thereof.

Structure 1: N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide

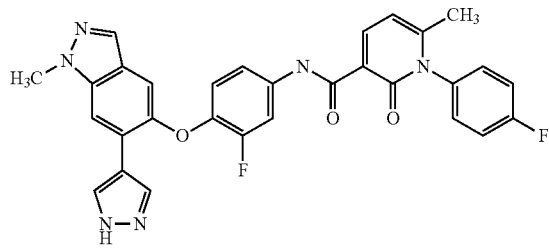 [SMILES: Cc1ccc(C(=O)Nc2ccc(Oc3cc4cnn(C)c4cc3-c3cn[nH]c3)c(F)c2)c(=O)n1-c1ccc(F)cc1]

Structure 2: 6-(1-Methyl-1H-pyrazol-4-yl)-3-(2-methyl-2H-indazol-5-ylthio)-[1,2,4]triazolo[4,3-b]pyridazine

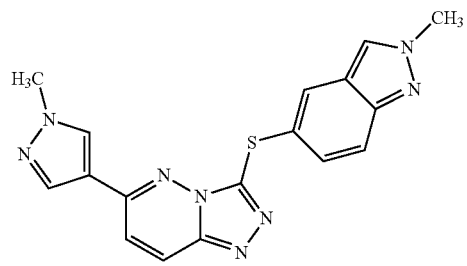 [SMILES: Cn1cc(-c2ccc3nnc(Sc4ccc5nn(C)cc5c4)n3n2)cn1]

Another aspect of this invention provides isolated nucleic acid molecules encoding the anti-c-Met antibodies of the invention, expression vectors comprising the nucleic acid molecules, and host cells comprising the nucleic acid molecules.

DEFINITIONS

Figure 1:
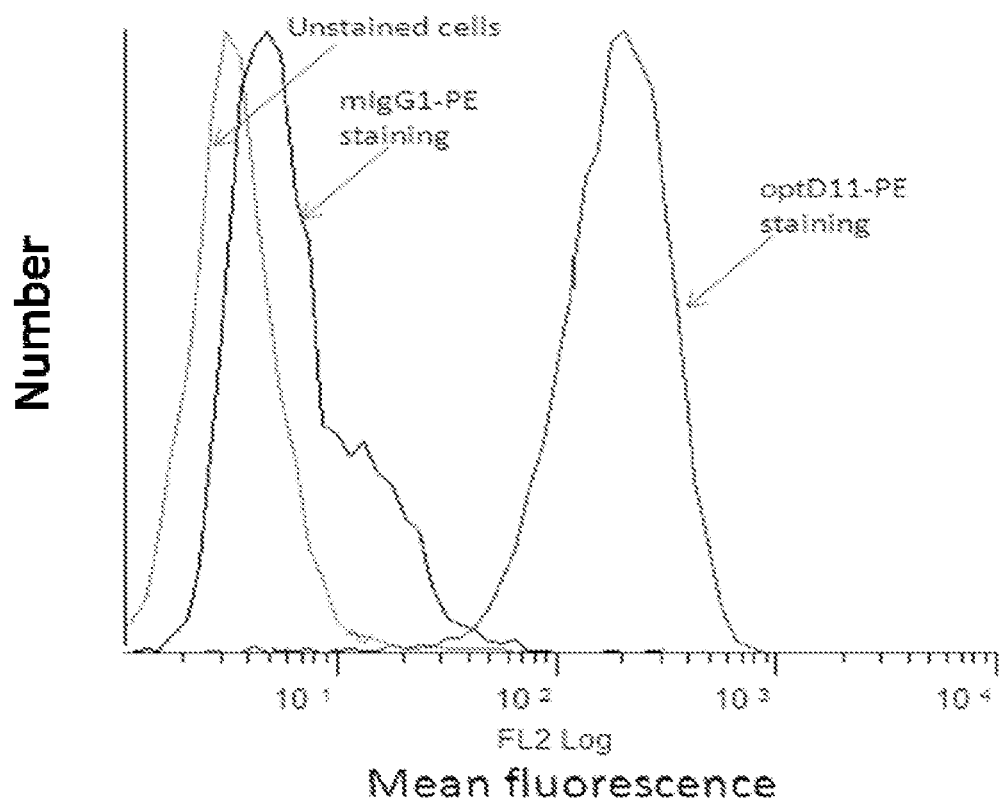
FIG. 1 shows FACS analysis of mAb OptD11 binding to cell surface c-Met in different tumor cells.

As used herein, "c-Met" or "human c-Met" refers to any human c-Met, unless otherwise indicated, as well as functionally active, mutated forms thereof. The structure of c-Met is depicted schematically as:

SEMA - PSI - 4 IPT - TM - JM - KD - intracellular tail

SEMA: Sema domain
PSI: Plexin, Semaphorins, and Integrins domain
IPT: 4 Immunoglobulins, Plexins, and Transcription factor domains
TM: Transmembrane region
JM: Juxtamembrane domain
KD: Kinase domain In the human c-Met ECD (SEQ ID NO: 19), amino acids 1-24 comprise the signal sequence. The mature protein begins at amino acid 25 of SEQ ID NO: 19. The SEMA domain consists of approximately 500 amino acid residues at the N-terminus of c-Met, and contains the α-chain (amino acid residues 25-307 of SEQ ID NO: 19, i.e., (SEQ ID NO: 20) and part of the β-chain (amino acid residues 308-519 of SEQ ID NO: 19, i.e., (SEQ ID NO: 21)).

As used herein, the term "antibody" refers to a monoclonal antibody, unless otherwise indicated. The term "monoclonal antibody", its abbreviation "mAb", and grammatical forms thereof are intended to refer to antibodies that are derived from a single copy or clone including, for example, any eukaryotic, prokaryotic, or phage clone, and not the method by which it is produced. Monoclonal antibodies of the invention preferably exist in a homogeneous or substantially homogeneous population. Complete mAbs contain two heavy chains and two light chains. "Antigen-binding fragments" of such monoclonal antibodies include, for example, Fab fragments, Fab' fragments, F(ab')$_2$ fragments, and single chain Fv fragments. Monoclonal antibodies and antigen-binding fragments thereof of the invention can be produced, for example, by recombinant technologies, phage display technologies, synthetic technologies, e.g., CDR-grafting, or combinations of such technologies, or other technologies known in the art. It is understood that regardless of whether antigen-binding fragments thereof are specified, the terms "antibody" and "monoclonal antibody" as used herein includes such fragments as well as single chain forms, unless indicated otherwise.

Methods for producing and purifying monoclonal antibodies and antigen-binding fragments thereof are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

The c-Met antibodies disclosed herein are useful for detecting expression, over-expression, or the level of c-Met present in or on cells, or in or on cells in tissues, organs, bodily fluids, etc., and in diagnostic, prognostic, and/or patient monitoring procedures. The term "bodily fluid" refers to any fluid or other material derived from the body of a normal or diseased subject, such as blood, blood serum, plasma, lymph, bone marrow, urine, saliva, tears, cerebrospinal fluid, milk, amniotic fluid, bile, urine, bronchial fluid, ascites fluid, pus, or any other biological product. Also included within the meaning of this term is an organ or tissue extract, and a culture fluid in which any cells or tissue preparation from a subject have been incubated.

The phrase "specifically binds" as used herein in reference to the affinity of a c-Met antibody for the ECD of human c-Met is intended to mean, unless indicated otherwise, a KD of less than about $1\times10^{-8}$ M, preferably, less than about $1\times10^{-9}$ M, more preferably, between about $1\times10^{-8}$ M and about $1\times10^{-11}$ M, even more preferably, between about $1\times10^{-9}$ M and about $5\times10^{-11}$ M, even more preferably, between about $5\times10^{-10}$ M and about $5\times10^{-11}$ M, even more preferably, between about 0.15 nM and about 0.05 nM, even more preferably, between about 0.15 nM and about 0.075 nM, and most preferably, about 0.10 nM, as determined by common methods known in the art, including by use of a SPR biosensor essentially as described herein.

The term "tumor" refers to all neoplastic cell growth and proliferation, whether malignant or benign, and all pre-cancerous and cancerous cells and tissues.

The terms "cancer" and "cancerous" refer to or describe the physiological condition in mammals typically characterized by aberrant cell growth/proliferation. Examples include but are not limited to: carcinoma, lymphoma, blastoma, sarcoma, and leukemia. The terms "cancer", "cancerous", and "tumor" are not mutually exclusive as used here.

As used herein, human c-Met is "over-expressed" in or on a human cell, CTC, or tumor tissue sample when the quantity of human c-Met is determined to be significantly greater for the human cell, CTC, or tumor tissue sample than the quantity of human c-Met in normal human cells or non-tumor human tissue.

Antibody Compositions and Methods

The c-Met monoclonal antibodies of the invention target c-Met in neoplasms regardless of tissue of origin. Because of the relatively greater expression of c-Met on tumor cells, it is possible to distinguish tumors from normal tissue. Also, because of the broad expression of c-Met across tumor classes (i.e., different organs and tissues of origin), imaging of c-Met as a surface marker is not specific to any particular tumor type, but can be generally used for any c-Met-expressing tumor.

There are well-known methods in the art that a skilled artisan may use to form stable, detectable antigen-antibody complexes (see, e.g., *Antibodies, A Laboratory Manual* by Harlow and Lane (current edition), Cold Spring Harbor Laboratory Press, Cold Spring Harbor, N.Y., for conditions permitting formation of detectable antigen/antibody complexes). In particular, WO 2010/059654 and/or U.S. Pat. No. 8,217,148 describes exemplary conditions which may permit the anti-c-Met monoclonal antibodies, or antigen-binding fragments thereof, of the present invention including, but not limited to the monoclonal antibody referred to herein as OptD11. A composition comprising an anti-c-Met monoclonal antibody of the present invention bound to the ECD of c-Met may also be detected, labeled, and/or identified using methods taught herein or generally known in the art, including, but not limited to, such methods disclosed in Harlow and Lane, ibid, or WO 2010/059654.

The anti-c-Met monoclonal antibodies of the present invention or the c-Met/anti-c-Met monoclonal antibody complexes described herein can be detectably labeled using any art-known means (see, e.g., *Antibody Engineering* Volume 2, Kontermann, Roland; Dübel, Stefan (Eds.)). Labels can be, for example, without limitation, light-emiting or light-absorbing agents, chromophores, chromogens, magnetic or iron particles, dyes, fluorescents, fluorophores, phosphorescents, chemiluminescents, bioluminescents agent, radionuclides, enzymes, positron emission tomographic-imageable agents, magnetic micro-beads, ferrofluid nanoparticles, secondary antibodies, and magnetic resonance-imageable agents.

Without limitation, c-Met or a detectably labeled c-Met/anti-c-Met monoclonal antibody complex can be on a cell, or fragment thereof, either in vivo, ex vivo or in vitro. For example, without limitation, such a cell or fragment thereof can be, in situ, isolated from its naturally occurring state, or in a sample, such as, e.g., from a cell pellet, xenograft, tissue (cancerous or non-cancerous), organ, bodily fluid, or any concentrated, purified, enriched form thereof. In any of these methods, the contacting and detecting can each be performed in vitro, the contacting can be performed in vivo and the detecting can be performed in vitro (or vice versa), or the contacting and the detecting can each be performed in vivo.

The term "detectably labeled" means that the anti-c-Met antibody, or antigen-binding fragment thereof of the present invention, or a complex of c-Met/anti-c-Met monoclonal antibody has attached to it, either covalently or non-covalently, a useful detectable label. In direct conjugate-labeled antibody methods, many different useful labels can be employed including, for example, prosthetic group complexes, chromophores, chromogens (color-producing substrates), dyes, fluorescent compounds, fluorogenic compounds, radioactive isotopes, paramagnetic isotopes, and compounds that can be imaged by positron emission tomography (PET) and magnetic resonance imaging (MRI). Other suitable labels are art-known or can be determined by routine experimentation. In indirect methods, a secondary antibody can be conjugated with, for example, an enzyme. Binding of the secondary antibody to the primary antibody, which is bound to the target antigen, can then be detected by reaction with a chromogenic substrate of the enzyme under appropriate conditions to yield a detectable signal.

Colorimetric detection can be used, employing chromogenic compounds that have, or result in, chromophores with high extinction coefficients, and which are therefore easily detectable. When later exposed to its substrate under appropriate reaction conditions, the enzyme will react with the substrate to produce a chemical moiety that can be detected, for example, by spectrophotometric, fluorometric, or visual means.

Enzymes commonly used for this purpose include horseradish peroxidase, alkaline phosphatase, glucose-6-phosphate dehydrogenase, malate dehydrogenase, staphylococcal nuclease, Δ-V-steroid isomerase, yeast alcohol dehydrogenase, α-glycerophosphate dehydrogenase, triose phosphate isomerase, asparaginase, glucose oxidase, β-galactosidase, ribonuclease, urease, catalase, glucoamylase, and acetylcholinesterase.

Examples of suitable prosthetic group complexes include, e.g., without limit, streptavidin/biotin and avidin/biotin.

Commonly used chromogens include diaminobenzidine (DAB); DAB with enhancement; 3-amino-9-ethyl carbazole (AEC); 4-chloro-1-naphthol (4-CN); Hanker-Yates reagent; alpha-naphthol pyronin; 3,3',5,5'-tetramethylbenzidine (TMB); Fast Blue BB; Fast Red TR; new fuchsin; BCIP-NBT; tetrazolium; tetranitroblue tetrazolium (TNBT); and immunogold with silver enhancement.

Use of chromogens is preferred because assays employing them can be easily performed in clinical diagnostic laboratories and reviewed by a pathologist with equipment commonly available in these laboratories.

An anti-c-Met monoclonal antibody herein conjugated to an enzyme can also be used in an enzyme-linked immunosorbent assays (ELISAs). Such assays are described in detail in, for example, Butler (1994) "ELISA" (Chapter 29), In: van Oss, C. J. et al., eds., *Immunochemistry*, Marcel Dekker, Inc., New York, pp. 759-803. The present c-Met antibodies can also be used in radioimmunoassay and fluorescence-activated cell sorting (FACS) analysis of cell-surface c-Met.

Useful fluorescent labels include umbelliferone, fluorescein, fluorescein isothiocyanate, dichlorotriazinylamine fluorescein, rhodamine, a dansyl group, phycoerythrin, phycocyanin, allophycocyanin, o-phthaldehyde, fluorescamine, and Cy5 (Haugland ((1996) *Handbook of Fluorescent Probes and Research Chemicals*, Sixth Ed., Molecular Probes, Eugene, Oreg.).

The anti-c-Met antibodies, or antigen-binding fragments thereof, or c-Met/anti-c-Met monoclonal antibody complexes of the present invention can also be detectably labeled using fluorescence-emitting metals such as $^{152}Eu^+$, or other members of the lanthanide series, by attaching them using such metal chelating groups as diethylenetriaminepentaacetic acid (DTPA) or ethylenediamine-tetraacetic acid (EDTA).

The anti-c-Met antibodies, or antigen-binding fragments thereof, or c-Met/anti-c-Met monoclonal antibody complexes of the present invention can also be detectably labeled by coupling them to a phosphorescent or chemiluminescent compound that can then be detected by the phosphorescence or luminescence that arises during the course of a chemical reaction. Examples of useful chemiluminescent compounds include luminol, isoluminol, theromatic acridinium ester, imidazole, acridinium salt, and oxalate ester. Likewise, a bioluminescent compound such as luciferin, luciferase, or aequorin can be used to label the antibody peptides. The presence of a bioluminescent protein is determined by detecting the presence of luminescence.

In vivo or in vitro imaging can be used to detect the proliferation, migration, or invasion of c-Met expressing or overexpressing tumor cells (and/or circulating tumor cells) in a patient, including occult metastases that are not observable by other methods. The expression of c-Met can be correlated with disease progression in cancer patients; patients with late stage cancer will usually have higher levels of c-Met expression in both their primary tumors and metastases. c-Met-targeted imaging could be used to stage tumors non-invasively, or to detect another disease associated with the presence of increased levels of c-Met.

The invention encompasses antibodies recombinantly fused or chemically conjugated (including both covalent and non-covalent conjugations) to a polypeptide (or portion thereof, preferably comprising at least: 10, 20, 30, 40, 50, 60, 70, 80, 90, or 100 contiguous amino acids of the polypeptide) to generate fusion proteins. The fusion does not necessarily need to be direct, but may occur through linker sequences.

Antibodies fused or conjugated to a polypeptide may also be used in in vitro immunoassays and in purification methods using known art methods (see, e.g., Harbor, et al., supra, and WO 93/2 1232; EP 439,095; Naramura et al. (1994) Immunol. Lett. 39:9 1-9; U.S. Pat. No. 5,474,981; Gillies, et al. 1992 PNAS 89:1428-32; Fell, et al. 1991 J. Immunol. 146: 2446-52).

The invention further includes compositions comprising a polypeptide (or fragment thereof) fused or conjugated to an antibody domain other than a variable region. Methods for fusing or conjugating a polypeptide (or fragment thereof) to an antibody or antibody portion are known (see, e.g., U.S. Pat. Nos. 5,336,603; 5,622,929; 5,359,046; 5,349,053; 5,447,851; 5,112,946; EP 307,434; EP 367,166; WO 96/04388; WO 91/06570; Ashkenazi, et al. (1991) PNAS 88: 10535-10539; Zheng, et al. (1995) J. Immunol. 154:5590-5600; and Vie, et al. (1992) PNAS 89: 11337-11341).

A polypeptide, polypeptide fragment, may be fused or conjugated to an antibody or antigen-binding fragment thereof described herein to increase the in vivo half-life. Further, a polypeptide, polypeptide fragment, may be fused or conjugated to an antibody or antigen-binding fragment thereof to facilitate purification. In preferred embodiments, the polypeptide is a hexa-histidine peptide, such as the tag provided in a pQE vector (QIAGEN, Inc., Chatsworth, Calif.), among others, many of which are commercially available. Hexa-histidine provides for convenient purification of a protein (Gentz, et al. (1989) PNAS 86:821-824). Other peptide tags useful for purification include, e.g., the "HA" tag, which corresponds to an epitope derived from the influenza hemagglutinin protein (see, e.g., Wilson, et al. (1984) Cell 37:767-778) and the "flag" tag.

The invention further encompasses antibodies or fragments thereof conjugated to a diagnostic or therapeutic agent. The antibodies can be used diagnostically to, for-example, monitor the development or progression of a tumor as part of a clinical testing procedure to determine the efficacy of a given treatment regimen. Detection can be facilitated by coupling the antibody to a detectable label. The detectable label may be coupled or conjugated either directly to the antibody (or fragment thereof) or indirectly, through an intermediate (such as, e.g., an art known linker) using established techniques (see, e.g., U.S. Pat. No. 4,741,900 for metal ions that can be conjugated to antibodies for use as diagnostics according to the invention).

A monoclonal antibody, or antigen-binding fragment thereof, of the invention can also be attached to solid supports, which are particularly useful for immunoassays or purification of a target antigen. Such solid supports include, e.g., without limitation, glass, cellulose, poly-acrylamide, nylon, polystyrene, polyvinyl chloride, or polypropylene. Techniques for conjugating a therapeutic moiety to an antibody are known, see, e.g., Arnon, et al., "Monoclonal Antibodies For Immunotargeting Of Drugs In Cancer Therapy", in Monoclonal Antibodies And Cancer Therapy, Reisfeld, et al. (eds.), pp. 243-56 (Alan R. Liss, Inc. 1985); Hellstrom, et al., "Antibodies For Drug Delivery", in Controlled Drug Delivery (2nd Ed.), Robinson, et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera, et al. (eds.), pp. 475-506 (1985); "Analysis, Results, and Future Prospective of the Therapeutic Use Of Radiolabeled Antibody in Cancer Therapy", in Monoclonal Antibodies for Cancer Detection and Therapy, Baldwin, et al. (eds.), pp. 303-16 (Academic Press 1985), and Thorpe, et al., "The Preparation and Cytotoxic Properties of Antibody-Toxin Conjugates," Immunol. Rev. 62: 119-58 (1982).

A particular protein such as c-Met can be measured by a variety of immunoassay methods including, e.g., without limitation, competitive and non-competitive assay systems using techniques such as, e.g., without limitation, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. For a review of immunological and immunoassay procedures in general, see Stites and Terr (eds.) (1991) *Basic and Clinical Immunology* (7th ed.). Moreover, the immunoassays of the invention can be performed in many configurations, which are reviewed extensively in Maggio (ed.) (1980) *Enzyme Immunoassay* CRC Press, Boca Raton, Fla.; Gosling J P 2000 *Immunoassays: A Practical Approach* (Practical Approach Series) Oxford Univ Press; Diamandis & Christopoulus, 1996 *Immunoassay* Academic Press, San Diego, Calif.; Tijan (1985) "Practice and Theory of Enzyme Immunoassays," *Laboratory Techniques in Biochemistry and Molecular Biology*, Elsevier Science Publishers B. V., Amsterdam; Wild, D. (Ed.), 2001 *The Immunoassay Handbook* (2nd edition) Nature Pub Group; James T. Wu, 2000 *Quantitative Immunoassay: A Practical Guide for Assay Establishment, Troubleshooting, and Clinical Application*, Amer Assn for Clinical Chemistry, Brousseau & Beaudet (Eds.) *Manual of Immunological Methods* CRC Press Boca Raton, Fla.; and Harlow and Lane *Antibodies, A Laboratory Manual*, supra. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays for measurement can be performed by a variety of art-known methods. In brief, immunoassays to measure the c-Met ECD can be either competitive or non-competitive binding assays. In competitive binding assays, the sample to be analyzed competes with a labeled analyte for specific binding sites on a capture agent bound to a solid surface. Preferably, the capture agent is an antibody specifically reactive with the c-Met ECD as described herein. The concentration of labeled analyte bound to the capture agent is inversely proportional to the amount of free analyte present in the sample.

In a competitive binding immunoassay, the target protein present in the sample (i.e., the c-Met ECD) competes with labeled protein for binding to an antibody, or antigen-binding fragment thereof, of the present invention. The antibody, or antigen-binding fragment thereof, of the present invention may be bound to a solid surface to effect separation of bound-labeled protein from the unbound-labeled protein. Alternately, the competitive binding assay may be conducted in liquid phase and a variety of techniques known in the art may be used to separate the bound-labeled protein from the unbound-labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding composition. This alteration in the labeled protein results in a decrease or increase in the signal emitted by label, so that measurement of the label at the end of the immunoassay allows for detection or quantitation of the protein.

Competitive assays are also particularly useful, where the cells are contacted and incubated with a labeled antibody having known binding affinity to the protein, such as $^{125}$I-antibody, and a test sample whose binding affinity to the binding composition is being measured. The bound and free-labeled binding compositions are then separated to assess the degree of protein binding. The amount of test compound bound is inversely proportional to the amount of labeled binding partner binding to the known source. Any one of numerous techniques can be used to separate bound from free protein to assess the degree of protein binding. This separation step could typically involve a procedure such as adhesion to filters followed by washing, adhesion to plastic followed by washing, or centrifugation of the cell membranes. Viable cells could also be used to screen for the effects of drugs on a c-Met mediated function (e.g., second messenger levels, such as, e.g., cell proliferation; inositol phosphate pool changes, transcription using a luciferase-type assay; and others). Some detection methods allow for elimination of a separation step, e.g., a proximity-sensitive detection system.

Qualitative or quantitative analysis of c-Met may also be determined by a variety of noncompetitive immunoassay methods using the antibodies, or antigen-binding fragments thereof, of the present invention. For example, a two-site, solid phase sandwich immunoassay may be used. In this type of assay, an antibody is attached to a solid support. A second protein-binding composition, which may also be an antibody, and which binds the protein at a different site, is labeled. After binding at both sites on the protein has occurred, the unbound-labeled binding composition is removed and the amount of labeled binding composition bound to the solid phase is measured. The amount of labeled binding composition bound is directly proportional to the amount of protein in the sample.

The ability of the antibody of interest to immunoprecipitate a particular antigen can be assessed by, e.g., Western blot analysis. One of skill in the art would be knowledgeable as to the parameters are modifiable to increase binding of an antibody to an antigen and to decrease background (e.g., by pre-clearing the cell lysate with sepharose beads). Further discussion of immunoprecipitation protocols can be found in, e.g., Ausubel et al, eds., 1994, Current Protocols in Molecular Biology, Vol. 1, John Wiley & Sons, Inc., New York.

An ELISA assay comprises preparing an antigen, coating the well of a 96 well microtiter-plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs, the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. An ordinary artisan can determine without undue experimentation what parameters to adjust, e.g., to increase signal as well as what other variations for an ELISA should be used (see, e.g., Ausubel, et al., eds., 1994, Current Protocols in Molecular Biology, Vol. 1, John Wiley & Sons, Inc., New York). For example, OptD11 may be useful as a c-Met ECD detection antibody for measuring total c-Met ECD in human tumors, tumor lysates, and bodily fluids such as blood if used in conjunction with a c-Met ECD capture antibody such a c-Met monoclonal antibody known in the art including, but not limited to, the c-Met monoclonal antibody known in the art as C8-H241 (see, for example, Chemical Abstracts Service #1365287-97-3). Alternatively, OptD11 may be useful as a c-Met ECD capture antibody for measuring total c-Met ECD in human tumors, tumor lysates, or bloodily fluids such as blood if used in conjunction with a c-Met ECD detection antibody such a c-Met monoclonal antibody known in the art including, but not limited to, the c-Met monoclonal antibody known in the art as C8-H241. Furthermore, OptD11 may be useful as a c-Met ECD capture antibody for measuring phosphor-c-Met in human tumors, tumor lysates, or bodily fluids such as blood if used in conjunction with a detection antibody such as an anti-phospho-tyrosine antibody conjugated to HRP (e.g., R&D Systems, Minneapolis, Minn.; catalog #841403) or an anti-phospho-c-Met pYpYpY1230/1234/1235 c-Met polyclonal antibody (e.g., Invitrogen, Carlsbad, Calif.; catalog #44-888G).

The binding affinity of an antibody to an antigen and the on- and off-rate of an antibody-antigen interaction can be determined by, e.g., using a competitive binding assay. One non-limiting example is a radioimmunoassay comprising incubating labeled antigen (e.g., using $^3$H or $^{125}$I) with an antibody of interest in the presence of increasing amounts of unlabeled antigen, and then detecting the amount of antibody bound to the labeled antigen. The affinity of the antibody of interest for a particular antigen and the binding off-rates can be determined from the data by, e.g., Scatchard plot analysis. Competition with a second antibody can also be determined using, e.g., radioimmunoassays.

Useful radiolabels, which are detected simply by gamma counter, scintillation counter, PET scanning, or autoradiography, include $^3$H, $^{124}$I, $^{125}$I, $^{131}$I, $^{35}$S, and $^{14}$C. For in vivo diagnosis, radionuclides can be bound to the mAb or antigen-binding fragments either directly or indirectly using a chelating agent such as DTPA and EDTA. Examples of such radionuclides include $^{99}$Tc, $^{123}$I, $^{125}$I, $^{131}$I, $^{111}$In, $^{97}$Ru, $^{67}$Cu, $^{67}$Ga, $^{68}$Ga, $^{72}$As, $^{89}$Zr, $^{90}$Y and $^{201}$Tl. Generally, the amount of labeled mAb needed for detectability in in vivo diagnostic use will vary depending on the patient's age, condition, sex, extent of disease, contraindications, if any, and other variables, and can be readily adjusted by the attending physician or diagnostician. A preferred diagnostic method is radioimmuno-scintigraphic analysis, which is preferably performed in a manner that results in serial total body gamma camera images, and allows determination of regional activity by quantitative "region-of-interest" (ROI) analysis.

In another embodiment, the monoclonal antibodies of the present invention may be used to detect circulating tumor cells (CTCs). CTCs are tumor cells that are shed from tumors, survive within the bloodstream during transit and initiate a new growth in distant sites. Detecting CTCs is useful as CTCs can be found in patients before a tumor is detected. Circulating tumor cells are also found in a significant proportion of patients when a carcinoma recurs, and CTCs persist in some patients after removal of the primary tumor. Evidence suggests that CTCs are derived from clones in the primary tumor as well as metastatic tumors and that they may reflect the tumor burden at all stages of tumor progression. Thus, in addition to a potential role in early diagnosis and prognostication, CTCs may play a major role in characterizing genetic and phenotypic changes with tumor progression, thereby helping to guide targeted therapy. More particularly, the anti-c-Met monoclonal antibodies of the present invention may be useful in assays that can capture, identify, and/or quantify CTCs such as, e.g., the CellSearch® CTC Test (Veridex LLC, San Diego, Calif.), Magnetic Activated Cell Sorting System (MACS®, Miltenyi Biotec GmbH, Germany), Dynal Magnetic Beads® (Invitrogen), EasySep® (Stem Cell Technologies, Vancouver Canada), CTC Chips (On-Q-ity, Waltham, Mass.), or any other test known in the art for the isolation and detection of CTCs such as those described in Sleijfer, et al. *Circulating tumour cell detection on its way to routine diagnostic implementation?* Eur J Cancer, 43 (18):2645-50 (2007); Lacroix M., *Significance, detection and markers of disseminated breast cancer cells.* Endocr Relat Cancer., 13 (4):1033-67 (2006); and Pantel, et al., *Detection, clinical relevance and specific biological properties of disseminating tumour cells.* Nat Rev Cancer, 8 (5):329-40 (2008)). Presently, CellSearch® CTC is the only diagnostic test approved by the USFDA as an automated test to detect and enumerate circulating tumor cells (Fed. Reg. 69(91):26036-38 (2004). Results from CellSearch® tests have been used to monitor disease progression and therapeutic efficacy in metastatic prostate (Danila, et al., *Circulating tumor cell number and prognosis in progressive castration-resistant prostate cancer.* Clin Cancer Res., 13(23):7053-58 (2007)), colorectal (Cohen, et al., *Isolation and characterization of circulating tumor cells in patients with metastatic colorectal cancer.* Clin Colorectal Cancer 6 (2):125-32 (2006)), and breast (Cristofanilli, et al. *Circulating tumor cells, disease progression, and survival in metastatic breast cancer.* N Engl J Med., 351(8):781-91 (2004)) cancer. The anti-c-Met antibody, or antigen-binding fragment thereof, of the present invention, e.g., OptD11, can be used in such methods, e.g. CellSearch® tests, and in some cases performed at the start of therapy and any time during the course of treatment for a c-Met-mediated-cancer. Preferably, an anti-c-Met antibody, or antigen-binding fragment thereof, of the present invention may be used in such methods along with antibodies specific for other polypeptides including, but not limited to, EPCAM, DAPI, CD45, and/or cytokeratin (including, but not limited to cytokeratin 7, 8, 18, and/or 19). Information generated from such testing may be useful for its prognostic value by allowing, e.g., monitoring of disease progression and therapeutic efficacy and may allow earlier (and ongoing) treatment decisions. Further, by permitting simultaneous binding of a detectably labeled antibody of the present invention and a therapeutic anti-c-Met antibody (such as disclosed in WO 2010/059654 and/or U.S. Pat. No. 8,217,148) a break in treatment with a therapeutic anti-c-Met antibody, for example, "washing out" the therapeutic antibody to allow the diagnostic antibody to bind c-Met, is not required. Consequently, an anti-c-Met antibody of the invention permits uninterrupted therapeutic treatment concomitantly with diagnostic monitoring, as necessary.

For in vivo applications, the detectably-labeled, anti-c-Met antibodies, or antigen-binding fragments thereof, of the invention can be formulated in convenient forms for administration. For diagnosis, the detectably labeled anti-c-Met antibodies, or antigen-binding fragments thereof, of the invention can be administered systemically, e.g., parenterally, by injection or infusion. Such injection or infusion can be by any known route, preferably intravenous injection or infusion, subcutaneous injection, intramuscular, intracranial, or intrathecal injection or infusion, or intraperitoneal administration. Injectables can be prepared in conventional forms, either as solutions or suspensions, or as solid forms. Such compositions can be prepared by methods well known in the art. See, e.g., *Remington: The Science and Practice of Pharmacy*, 19$^{th}$ ed. (1995), A. Gennaro et al., Mack Publishing Co., and comprise anti-c-Met antibodies disclosed herein, and a pharmaceutically or diagnostically acceptable carrier, diluent, or excipient.

Dosage can vary from 0.01 mg/kg to 100 mg/kg body weight. Further guidance regarding appropriate doses for diagnostic imaging can be found in Smith et al. (1977) *Antibodies in Human Diagnosis and Therapy*, Haber et al., eds., Raven Press, New York, pages 365-389.

For in vivo c-Met detection purposes, the term "effective amount" of the present anti-c-Met monoclonal antibody, or antigen-binding fragment thereof, refers to the amount of antibody compound which, upon single or multiple dose administration to a patient, provides the ability to detect c-Met in vivo.

Articles of Manufacture and Kits

The invention also provides articles of manufacture and kits containing compositions useful for diagnosing, detecting, quantifying, and/or imaging c-Met-positive tumors and non-cancerous cells. The article of manufacture may comprise a container with a label. The container may holds a composition comprising the anti-c-Met monoclonal antibody, or antigen-binding fragment thereof, of the invention, which is either detectably labeled, or unlabeled. The label on the container may indicate that the composition is used for prognosing or monitoring cancer, or for diagnosing or monitoring particular types of cancer or tumors that express c-Met or for which c-Met levels or turnover is prognostic, or for prediction of an effective target for therapy. In another embodiment, the label may indicate that the composition is useful for detecting and/or quantifying c-Met, and can also indicate directions for either in vivo or in vitro use.

The kit of the invention can also comprise a container comprising a secondary antibody or even a c-Met antigen, preferably antigen comprises the extracellular domain (ECD) of human c-Met consisting of the amino acid sequence as in SEQ ID NO: 19. The secondary antibody can be conjugated with an enzyme. A chromogenic substrate of the enzyme can also be included in the kit. The kit may further include other materials desirable from a commercial and user standpoint, including buffers, diluents, filters, needles, syringes, and package inserts with instructions for use in vivo, in vitro, or both.

Aberrant HGF and/or c-Met signaling is inversely correlated with clinical outcome, and has been documented in a wide range of human malignancies. Inappropriate expression of c-Met correlates with poor patient prognosis in many human tumors. The present monoclonal antibody and antigen-binding fragments thereof that bind c-Met useful in diagnostic procedures can be used to identify and stratify cancer patients, and to monitor patient responses to c-Met targeted therapy by using tissue samples collected by routine standards, and which impose minimum patient discomfort.

The present methods thus offer newly diagnosed cancer patients a form of metastatic risk stratification that uses non-invasive means to assess as high or low the probability that a given tumor will subsequently invade or metastasize, without any dependence on the tumor's tissue of origin. Such information improves the ability to design appropriate monitoring and therapy protocols on an individual patient basis.

The c-Met antibodies or c-Met/anti-c-Met monoclonal antibody complexes of the present invention and methods disclosed herein can be used in the diagnosis of a variety of mammalian species, and are equally applicable in the practice of human or veterinary medicine. Thus, these antibodies, complexes, and methods may be used with domestic and commercial animals, and most preferably, with humans.

Another aspect of this invention pertains to isolated nucleic acid molecules encoding any of the aforementioned anti-c-Met antibodies, expression vectors comprising the nucleic acid molecules, and host cells comprising the nucleic acid molecules. The invention further provides methods of purifying any of the aforementioned anti-c-Met antibodies.

Preferred host cells for transformation of vectors and expression of the antibodies of the present invention are mammalian cells, e.g., NS0 cells (non-secreting (0) mouse myeloma cells), 293, SP20 and CHO cells and other cell lines of lymphoid origin such as lymphoma, myeloma, or hybridoma cells. Other eukaryotic hosts, such as yeasts, can be alternatively used.

An "isolated" antibody in reference to an anti-c-Met antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, an antibody of the present invention will be purified (1) to greater than 95%0/by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. The term "isolated" in reference to an anti-c-Met antibody of the present invention may include the antibody in situ within recombinant cells since at least one component of the antibody's natural environment will not be present. The anti-c-Met antibodies of the present invention may be isolated or purified by any method known in the art, including precipitation by ammonium sulfate or sodium sulfate followed by dialysis against saline, ion exchange chromatography, affinity or immuno-affinity chromatography including, but not limited to, Protein-A affinity chromatography, as well as gel filtration or zone electrophoresis.

Additionally, the present invention provides expression vectors containing the polynucleotide sequences previously described operably linked to a control sequence such as an expression sequence, a promoter and/or an enhancer sequence. A variety of expression vectors for the efficient synthesis of antibody polypeptide in prokaryotic systems, such as bacteria and eukaryotic systems, including but not limited to, yeast and mammalian cell culture systems have been developed. The vectors of the present invention can comprise segments of chromosomal, non-chromosomal and synthetic DNA sequences.

The present invention also provides recombinant host cells containing the recombinant vectors previously described. Antibodies of the present invention can be expressed in cell lines other than in hybridomas. Nucleic acids, which comprise a sequence encoding an antibody according to the invention, can be used for transformation of a suitable mammalian host cell.

Cell lines of particular preference are selected based on high levels of expression, constitutive expression of protein of interest and minimal contamination from host proteins. Mammalian cell lines available as hosts for expression are well known in the art and include many immortalized cell lines, such as but not limited to, COS-7 cells, Chinese Hamster Ovary (CHO) cells, Baby Hamster Kidney (BHK) cells and many others including cell lines of lymphoid origin such as lymphoma, myeloma, or hybridoma cells.

EXAMPLE 1

Antibody Expression and Purification

The anti-c-Met antibodies of the present invention, including, but not limited to OptD11, may be transiently expressed in HEK293 EBNA cells (Edge BioSystems, Gaithersburg, Md.) using standard transfection procedures. Transfected cells are cultured in standard serum-free medium containing geneticin (G418) and tobramycin for 48 to 120 hours at 37° C. after transfection. The anti-c-Met antibody may be purified on a 60 ml rProtein A Sepharose column (for example, GE Healthcare, Piscataway, N.J.; catalog #17-1279-04) by following the manufacturer's instructions, and further concentrated and purified by size exclusion chromatography (XK50/60 Superdex200, GE Healthcare) with phosphate buffered saline (PBS), pH 7.4, as the mobile phase. Next, the antibody preparation may be filtered using a Millev-GV, PVDF membrane, 0.22 µm, 33 mm, (Millipore; #SLGV033RS) and stored at 4 to 8° C.

TABLE 1

CDR Amino Acid Sequences of Antibody OptD11

| CDRs | Amino Acid Sequences |
|---|---|
| OptD11 LCDR 1 | SVSSSISSTNLH (SEQ ID NO: 1) |
| OptD11 LCDR 2 | GTSNLAS (SEQ ID NO: 2) |
| OptD11 LCDR 3 | QQWSSYPYT (SEQ ID NO: 3) |
| OptD11 HCDR 1 | GYTFTSRYIH (SEQ ID NO: 4) |
| OptD11 HCDR 2 | WIYPVTGDTYYNEKFKG (SEQ ID NO: 5) |
| OptD11 HCDR 3 | GGGMFYY (SEQ ID NO: 6) |

EXAMPLE 2

Binding Kinetics and Affinity of Antibody OptD11

The extracellular domains (ECDs) of human and cynomolgus monkey c-Met sequences may be expressed as Fc fusion proteins with a flag- and His-tag (Flis-tag) at the C-terminus of the Fc, as in SEQ ID NOs: 17 and 18. These c-Met ECD Fc fusion proteins may be transiently expressed in HEK293 EBNA separately and purified essentially as described in Example 1.

The binding kinetics of an anti-c-Met monoclonal antibody of the invention to human and/or cynomolgus monkey c-Met ECDs may be determined by use of a surface plasmon resonance biosensor such as a BIAcore® 2000, BIAcore® 3000, or a BIAcore® T100 (GE Health Care, Piscataway, N.J.) according to methods known in the art. Except as noted, all reagents and materials may be purchased from Biacore®, and measurements may be performed at 25° C.

Briefly described, the anti-c-Met monoclonal antibody of the invention may be dissolved in HBS-EP buffer (150 mM sodium chloride, 3 mM EDTA, 0.005% (w/v) surfactant P-20, and 10 mM N-2-hydroxyethylpiperazine-N'-2-ethanesulfonic acid (HEPES) at pH 7.4; #BR-1001-88). Goat anti-mouse Fc antibody is immobilized on flow cells 1 to 4 of a CM5 sensor chip at a level of 4000 response units (RUs) using amine coupling chemistry to capture anti-c-Met antibodies.

Binding may be evaluated using multiple analytical cycles. Each cycle is performed at a flow rate of 50 µl/minute, and may consist of the following steps: injection of about 10 µl of an anti-c-Met monoclonal antibody at 10 µg/ml aiming at a capture of 40-100 RUs, injection of 250 µl of human or cynomolgus monkey c-Met-Flis-Fc ECD (starting at 100 nM and using two-fold serial dilutions for each cycle) followed by 20 minutes for dissociation, and regeneration using about 30 µl of 10 mM glycine hydrochloride, pH 1.5. Association and dissociation rates for each cycle may be evaluated using a "1:1 (Langmuir) binding" model in the BIAevaluation software 4.1.

The anti-c-Met monoclonal antibody of the present invention, OptD11, was tested for its binding kinetics to the ECD of human and cynomolgus monkey c-Met expressed as Fc fusion proteins with a flag- and His-tag (Flis-tag) at the C-terminus of the Fc, as in SEQ ID NOs:17 and 18. As shown in Table 2, OptD11 binds human and cynomolgus monkey c-Met-Flis-Fc ECDs with very high binding affinity ($K_d$). Table 2 also displays $k_{on}$ and $k_{off}$ rate data.

TABLE 2

Binding Kinetics and Affinity of Antibody OptD11

| ECD | $k_{on}$ ($10^5$ 1/Ms) | $k_{of}$ ($10^{-4}$ 1/s) | $K_d$ (nM) |
|---|---|---|---|
| Human c-Met | 1.6 ± 0.5 | 0.09 ± 0.12 | 0.12 ± 0.07 |
| Cynomolgus Monkey c-Met | 1.3 ± 0.3 | 0.47 ± 0.14 | 0.35 ± 0.04 |

EXAMPLE 3

Detection of c-Met on Cell Surfaces by FACS Analysis Using mAb OptD11

An in vitro assay designed to measure cell surface c-Met receptor may be conducted to determine if the c-Met antibodies are capable of staining both human and cynomolgus monkey c-Met on the cell surface. A secondary anti-mouse-IgG1 antibody with Alexa Fluor 488 labeling may be used in this assay to detect the cell surface c-Met receptors by fluorescence-activated cell surface (FACS) analysis.

Briefly described, six-well tissue culture plates may be seeded with MKN45 cells (human gastric tumor cells that over-express c-Met; Japan Tumor Bank; #JCRB0254) at 1.5× $10^5$ cells/well/2 ml in RPMI-1640 medium (Life Technologies, Grand Island, N.Y.; catalog #11835); 10% FBS (Life Technologies; catalog #10082); 2 mM L-glutamine (Life Technologies; catalog #25030); 100 U/500 mL penicillin G and 100 µg/500 mL streptomycin (Life Technologies; catalog #15140). Plated cells may be incubated for 24 hours at 37° C., 95% relative humidity, 5% (v/v) $CO_2$. NIH 3T3 cells (ATCC; #CRL-1658) may be cultured in DMEM (Life Technologies; catalog #11995); 10% calf serum (Life Technologies; catalog #30-2030); 2 mM L-glutamine (Life Technologies; catalog #25030); 100 U/500 mL penicillin G and 100 µg/500 mL streptomycin (Life Technologies; catalog #15140).

The cynomolgus monkey c-Met may be introduced into NIH 3T3 cells by retroviral-mediated gene transfer, and several stable clones over-expressing cyno c-Met can be established. NIH 3T3-cyno-c-Met cells may be cultured in six well tissue culture plates to 80% confluency. 1 ml of enzyme-free cell dissociation solution (EMD Millipore, Billerica, Mass.; catalog #S-014-B) may be added to each well, and left for 5 min. at room temperature to disperse cells. Next, the cells may be pipetted up and down, and collected into centrifuge tubes. The cells may be washed once in culture medium followed by one more wash in binding buffer (Dulbecco's phosphate buffered saline (DPBS)/1% bovine serum albumin (BSA)/0.01% sodium azide). The c-Met antibody may be labeled with Alexa Fluor 488 using an Alexa Fluor 488 Monoclonal Antibody Labeling Kit (Molecular Probes, Eugene, Oreg.; catalog #A-20181) according to the manufacturer's instructions. Cell surface c-Met receptors may be stained with 100 μl of binding buffer containing 2 μg/ml of Alexa Fluor 488-labeled c-Met antibody for 60 min. on ice. Next, the cells may be washed once with binding buffer and resuspended in DPBS containing 2 μg/ml propidium iodide (PI; for staining the dead cells). The cell surface c-Met receptors on the live cells may be analyzed by FACS analysis, and 10,000 events may be acquired for each sample. For data analysis, the mean fluorescence may be used to compare anti-c-Met antibody-treated samples with IgG isotype-treated controls.

In FACS analysis of c-Met expression on cell surfaces performed essentially as described in this Example, the OptD11 c-Met antibody stains cell surface c-Met on human tumor cells as well as cynomolgus monkey c-Met expressed on NIH 3T3 cells. Therefore, OptD11 antibodies can be used to stain cell surface c-Met from fluid of tumor biopsies, permitting FACS analysis of such samples.

These data indicate that OptD11 c-Met antibody can be used to detect cell surface c-Met receptor levels for diagnostic and prognostic purposes, and for optimizing c-Met targeted therapies for the treatment of cancer.

EXAMPLE 4

Human c-Met ECD ELISA Using mAb OptD11

The in vitro binding of OptD11 mAb to human c-Met ECD may be determined by measuring the reactivity of the antibody to human c-Met ECD proteins in an enzyme-linked immunosorbent assay (ELISA).

Briefly described, the wells of a 96-well microtiter ELISA plate (Greiner Bio-One GmbH; catalog #655081) may be coated with a c-Met capture antibody that specifically binds to an epitope within the c-Met ECD α-chain (e.g., SEQ ID NO: 20) and/or β-chain (e.g., residues 1-67 or 1-92 of SEQ ID NO: 21). More particularly, the c-Met capture antibody can be diluted to 2 μg/ml in 1× of commercially available coating buffer (for example, BioFX catalog #COAT-1000-01 from SurModics IVD (Eden Prairie, Minn.)). Approximately, 110 μL of the diluted c-Met capture antibody may be added to each well of the 96-well microtiter ELISA plate. Then the plate(s) can be covered and incubated overnight at 4° C. After the overnight incubation at 4° C., the wells may be aspirated and washed two times with 200 μL wash buffer (BioFX; catalog #WSH-1000-01) using an automatic plate-washer. Next, approximately 200 μL blocking buffer (1× wash buffer+2% BSA) (Sigma-Aldrich Co., St. Louis, Mo., catalog #A7979) may be added to each well of the ELISA plate and incubated 1 hour at room temperature. Next, the wells of the plates may be washed two times with approximately 200 μL wash buffer using an automatic plate-washer. One hundred microliters (μL) of serially diluted (in an acceptable diluent, e.g., blocking buffer) ECD of human c-Met expressed as a Fc fusion protein with a flag- and His-tag (Flis-tag) at the C-terminus of the Fc (as shown in SEQ ID NO: 17, for example) may be added to the ELISA plate(s) and incubated for 2 hours with shaking at room temperature. The serial dilutions may start at 1280 pg/mL with 2-fold dilution down to 20 μg/mL, for example. Next, 100 μL of 0.5 μg/mL biotinylated OptD11 c-Met antibody (in an acceptable diluent, e.g., blocking buffer) may be added as the c-Met detection antibody and incubated 2 hours with shaking at room temperature. The plates may then be aspirated and washed 4 times with wash buffer using automatic plate-washer. Next, 100 μL of 83 ng/mL peroxidase conjugated streptavidin (Jackson Immunoresearch, West Grove, Pa.; catalog #016-030-084) in diluent may be added to all the wells and the plates may be incubated two hours with shaking at room temperature. Next the wells of the plates may be aspirated and washed 6 times with wash buffer using automatic plate-washer. After the plates are washed, 100 μL of TMB (BioFX catalog #TMBW-1000-01) may be added to each well and the plates may be incubated for 10 minutes at room temperature. To stop the reaction, 100 μL of stop solution may be added to each well (BioFX; catalog #LSTP-1000-01). The colorimetric signals may be developed and read using a plate reader at 450 nm with 570 nm correction.

Figure 2:
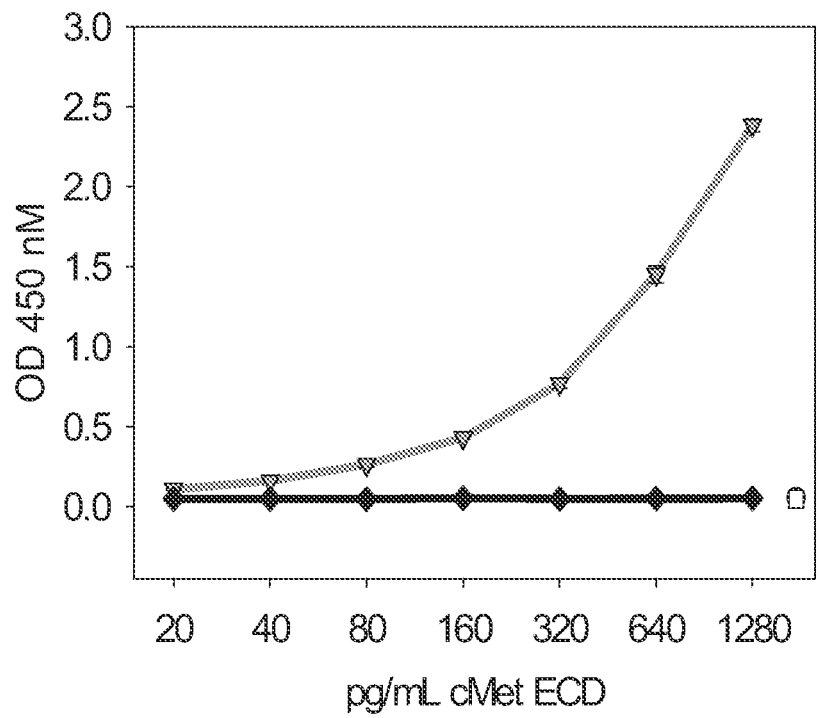
FIG. 2 shows, in graph format, a binding curve for soluble c-Met ECD-Fc fusion protein by solid-phase ELISA using the anti-c-Met therapeutic antibody C8-H241 (human IgG4 subtype) as a c-Met capture antibody and biotinylated mAb OptD11 (murine IgG1 subtype) as a c-Met detection antibody reagent.

The monoclonal antibody OptD11 was tested for binding to recombinant human c-Met ECD protein fused to Fc in an ELISA essentially as described above. More specifically, using the anti-c-Met antibody C8-H241 (human IgG4 subtype) as c-Met capture antibody and biotinylated mAb OptD11 as the c-Met detection antibody reagent, mAb OptD11 provides high sensitivity (detects c-Met ECD as low as 20 pg/ml) as well as a wide range of c-Met ECD detection (i.e., 20 pg/ml to 1280 pg/ml) (see FIG. 2). The results of the ELISA experiment indicate that OptD11 binds to a recombinant human c-Met ECD fusion protein and may be useful in in vitro immunochemical methods including, but not limited to, ELISA, for detecting the ECD of c-Met receptor for diagnostic, prognostic and predictive purposes.

EXAMPLE 5 mAb OptD11 and mAb C8-H241 Simultaneously Bind ECD of Human c-Met

To determine if an anti-c-Met antibody of the invention (such as OptD11) can bind the ECD of human c-Met at the same time as an anti-c-Met therapeutic antibody (such as, e.g., C8-H241, disclosed in WO 2010/059654 and/or U.S. Pat. No. 8,217,148), a binding experiment may be performed using a surface plasmon resonance biosensor such as a BIAcore® 2000, BIAcore® 3000, or a BIAcore® T100 (GE Health Care, Piscataway, N.J.) according to methods known in the art. Except as noted, all reagents and materials may be purchased from BIAcore®. All reagents and materials may be purchased from BIAcore® unless otherwise noted. All measurements may be performed at 25° C. using HBS-EP (150 mM sodium chloride, 3 mM EDTA, 0.005% (w/v) surfactant P-20, and 10 mM HEPES, pH 7.4) as both a running and sample buffer. Mouse IgG1 anti-polyhistidine antibody (R&D systems, Mab050) may be immobilized on flow cells 1 to 4 of a CM5 sensor chip at a level of 7000 response units (Rus) using an amine coupling kit. Next, human c-Met-ECD-Fc-Flis may be injected to flow cell 2 then an anti-c-Met antibody (500 nM), such as mAb C8-H241, may be injected through flow cell 1 and 2 (50 μL/min for 5 minutes). By the end of injection, binding may be saturated and a binding response unit may be used to calculate binding stoichiometry.

Figure 3:
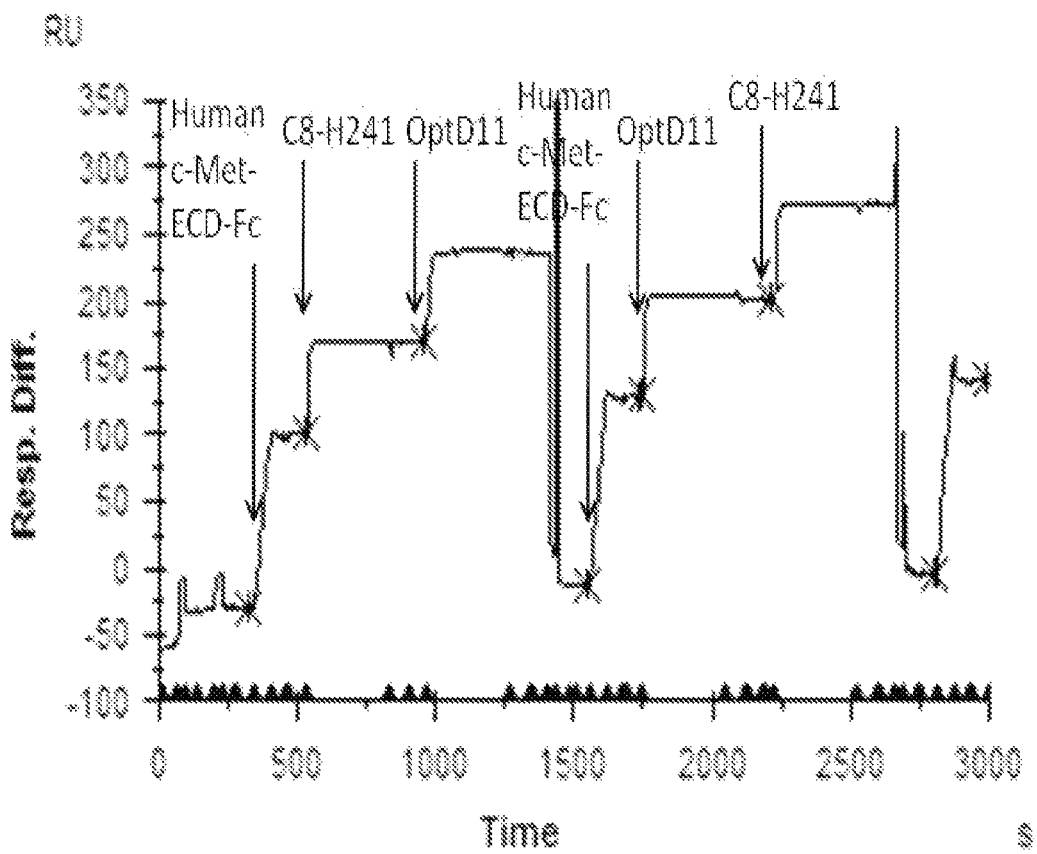
FIG. 3 illustrates the simultaneous but non-competitive binding of mAb C8-H241 (human IgG4 subtype) and OptD11 to human c-Met-ECD-Fc-Flis fusion protein as determined by use of a surface plasmon resonance biosensor.

In experiments performed essentially as described in this Example 5, each c-Met-ECD-Fc-Flis dimer binds 0.9 C8-H241 (human IgG4 subtype) anti-c-Met antibodies. Upon subsequent injection of mAb OptD11 (mouse IgG1 subtype) additional binding to c-Met-ECD-Fc-Flis was observed (see FIG. 3). The stoichiometry of the additional binding was also approximately 0.9, indicating that anti-c-Met mAb OptD11 (mouse IgG1 subtype) also fully binds c-Met-ECD-Fc-Flis that is bound by anti-C-met mAb C8-H241 (human IgG4 subtype).

In order to determine whether simultaneous binding of anti-c-Met mAbs C8-H241 (human IgG4 subtype) and OptD11 (mouse IgG1 subtype) to human c-Met-ECD-Fc-Flis is independent of binding order, the chip surface was regenerated to remove c-Met-ECD-Fc-Flis and both c-Met antibodies before repeating the binding cycle. An additional cycle of binding was repeated as described above, however, the binding order of the antibodies was reversed (i.e., mAb OptD11 before mAb C8-H241). Similar results were obtained (see FIG. 3).

These data show that mAb OptD11 (mouse IgG1 subtype) and mAb C8-H241 (human IgG4 subtype) can simultaneously bind human c-Met-ECD-Fc-Flis. Furthermore, the data strongly suggests that the epitopes of these two anti-c-Met antibodies differ.

We claim:

1. An antibody, or an antigen-binding Fab fragment thereof, that specifically binds to the extracellular domain (ECD) of mature human c-Met consisting of amino acids 25-932 of SEQ ID NO: 19, the antibody or the Fab fragment comprising:
   i. light chain complementarity determining regions LCDR1, LCDR2, and LCDR3 consisting of the amino acid sequences SVSSSISSTNLH (SEQ ID NO: 1), GTSNLAS (SEQ ID NO: 2), and QQWSSYPYT (SEQ ID NO: 3), respectively; and
   ii. heavy chain complementarity determining regions HCDR1, HCDR2, and HCDR3 consisting of the amino acid sequences GYTFTSRYIH (SEQ ID NO: 4), WIYPVTGDTYYNEKFKG (SEQ ID NO: 5), and GGGMFYY (SEQ ID NO: 6), respectively.

2. The antibody, or the Fab fragment, of claim 1 comprising:
   i. a light chain variable region (LCVR) comprising the amino acid sequence as in SEQ ID NO: 7; and
   ii. a heavy chain variable region (HCVR) comprising the amino acid sequence as in SEQ ID NO: 9.

3. The antibody of claim 1 or 2 comprising:
   i. a light chain comprising the amino acid sequence as in SEQ ID NO: 11; and
   ii. a heavy chain comprising the amino acid sequence as in SEQ ID NO: 13.

4. The antibody of claim 3 comprising:
   i. two light chains; and
   ii. two heavy chains, wherein each of the light chains consist of the amino acid sequence as in SEQ ID NO: 11 and each of the heavy chains consist of the amino acid sequence as in SEQ ID NO: 13.

5. The antibody or the Fab fragment of claim 1 or 2, further comprising a detectable label.

6. The antibody of claim 4, further comprising a detectable label.

7. A composition comprising:
   a. an antibody, or an antigen-binding Fab fragment thereof, that specifically binds to the extracellular domain (ECD) of mature human c-Met consisting of amino acids 25-932 of SEQ ID NO: 19, the antibody or the Fab fragment comprising:
      i. light chain complementarity determining regions LCDR1, LCDR2, and LCDR3 consisting of the amino acid sequences SVSSSISSTNLH (SEQ ID NO: 1), GTSNLAS (SEQ ID NO: 2), and QQWSSYPYT (SEQ ID NO: 3), respectively; and
      ii. heavy chain complementarity determining regions HCDR1, HCDR2, and HCDR3 consisting of the amino acid sequences GYTFTSRYIH (SEQ ID NO: 4), WIYPVTGDTYYNEKFKG (SEQ ID NO: 5), and GGGMFYY (SEQ ID NO: 6), respectively, and b. a diagnostically acceptable carrier, diluent, or excipient.

8. The composition of claim 7, wherein the antibody or the Fab fragment comprises:
  i. a light chain variable region (LCVR) comprising the amino acid sequence as in SEQ ID NO: 7; and
  ii. a heavy chain variable region (HCVR) comprising the amino acid sequence as in SEQ ID NO: 9.

9. A composition comprising the antibody or the Fab fragment of claim 1 or 2 and a polypeptide comprising the ECD of mature human c-Met consisting of amino acids 25-932 of SEQ ID NO: 19, wherein the antibody or the Fab fragment is bound to the polypeptide.

10. The composition of claim 9, wherein the antibody or the Fab fragment is bound to the polypeptide comprising the ECD of mature human c-Met at an epitope within the amino acid sequence as in SEQ ID NO: 15 or 16.

11. A kit comprising a container comprising the antibody or Fab fragment of claim 1 or 2.

12. The kit of claim 11 further comprising a container comprising a secondary antibody that binds to the antibody or the Fab fragment; and, optionally, instructions for using the antibody or the Fab fragment, with or without the secondary antibody, to detect c-Met.

13. The kit of claim 12, wherein said secondary antibody is conjugated to an enzyme.

14. The kit of claim 13, further comprising a container having a chromogenic substrate of said enzyme.

15. The antibody or the Fab fragment of claim 2 for use in an assay to a) identify cancer patients with tumor cells expressing c-Met and/or 2) monitor a cancer patient's response to treatment with an anti-c-Met therapeutic antibody or an anti-c-Met chemotherapeutic agent.

16. A method of detecting c-Met expressed by a human cell, the method comprising:
  (a) contacting said cell with an antibody, or an antigen-binding Fab fragment thereof, that specifically binds to the ECD of mature human c-Met consisting of amino acids 25-932 of SEQ ID NO: 19, the antibody or the Fab fragment comprising:
    i. light chain complementarity determining regions LCDR1, LCDR2, and LCDR3 comprising the amino acid sequences SVSSSISSTNLH (SEQ ID NO: 1), GTSNLAS (SEQ ID NO: 2), and QQWSSYPYT (SEQ ID NO: 3), respectively; and
    ii. heavy chain complementarity determining regions HCDR1, HCDR2, and HCDR3 comprising the amino acid sequences GYTFTSRYIH (SEQ ID NO: 4), WIYPVTGDTYYNEKFKG (SEQ ID NO: 5), and GGGMFYY (SEQ ID NO: 6), respectively, for a time and under conditions that permit said antibody or the Fab fragment to bind to the ECD;
  (b) optionally, removing any non-specifically bound antibody or Fab fragment; and
  (c) detecting and/or quantifying the amount of the antibody or the Fab fragment which is specifically bound to the ECD.

17. A method of selecting a patient having a tumor suitable for treatment with an anti-c-Met therapeutic antibody or an anti-c-Met chemotherapeutic agent, comprising:
  (a) contacting at least one cell from said tumor with an antibody, or an antigen-binding Fab fragment thereof, that specifically binds to the ECD of mature human c-Met consisting of amino acids 25-932 of SEQ ID NO: 19, the antibody or the Fab fragment comprising:
    i. light chain complementarity determining regions LCDR1, LCDR2, and LCDR3 comprising the amino acid sequences SVSSSISSTNLH (SEQ ID NO: 1), GTSNLAS (SEQ ID NO: 2), and QQWSSYPYT (SEQ ID NO: 3), respectively; and
    ii. heavy chain complementarity determining regions HCDR1, HCDR2, and HCDR3 comprising the amino acid sequences GYTFTSRYIH (SEQ ID NO: 4), WIYPVTGDTYYNEKFKG (SEQ ID NO: 5), and GGGMFYY (SEQ ID NO: 6), respectively, for a time and under conditions that permit said antibody, or the Fab fragment, to bind to the ECD;
  (b) optionally, removing any non-specifically bound antibody or Fab fragment; and
  (c) detecting and/or quantifying the amount of antibody or Fab fragment which is specifically bound to the ECD, wherein the presence of the antibody or Fab fragment specifically bound to the ECD identifies the patient as being appropriate for treatment with said anti-c-Met therapeutic antibody or said an anti-c-Met chemotherapeutic agent.

18. The method of claim 16 or 17, wherein said cell is an isolated cell, or is present in a cell pellet, a xenograft sample, a tissue sample, an organ sample, or a bodily fluid sample.

19. A kit comprising the antibody or Fab fragment of claim 1 or 2 for:
  (a) detecting and/or quantifying c-Met in or on a cell;
  (b) detecting and/or quantifying c-Met expressing tumor cells in a patient;
  (c) detecting and/or quantifying c-Met expressing circulating tumor cells in a blood sample of a patient;
  (d) detecting and/or quantifying c-Met expressing tumor cells in a bodily fluid from a cancer patient such as in blood, blood serum, urine, ascites fluid, lymphatic fluid, spinal fluid, and bronchial fluid;
  (e) assessing whether an individual has, or is at risk for developing, cancer of a tissue or organ wherein c-Met is expressed or over-expressed;
  (f) selecting a patient having a tumor suitable for treatment with an anti-c-Met therapeutic antibody or chemotherapeutic agent; or
  (g) determining response to treatment with an anti-c-Met therapeutic antibody or an anti-c-Met chemotherapeutic agent.

20. A method of determining a patient's response to the administration of an anti-c-Met therapeutic antibody or an anti-c-Met chemotherapeutic agent, comprising:
  (a) contacting at least one cell from said patient's tumor with the antibody or Fab fragment of claim 1 or 2 for a time and under conditions that permit said antibody or the Fab fragment to bind to the ECD of mature human c-Met;
  (b) optionally, removing any non-specifically bound antibody or Fab fragment; and
  (c) detecting and/or quantifying the amount of the antibody or Fab fragment which is specifically bound to the ECD of mature human c-Met, wherein a patient's response to the administration of the anti-c-Met therapeutic antibody or the anti-c-Met chemotherapeutic agent is determined based on the amount of the antibody or Fab fragment of claim 1 specifically bound to the ECD of mature human c-Met.

21. A method of measuring a patient's response to the administration of an anti-c-Met therapeutic antibody or an anti-c-Met chemotherapeutic agent, comprising:
  (a) contacting at least one cell from a patient's tumor with the antibody or the Fab fragment of claim 1 or claim 2 both (i) prior to and (ii) after administration of an anti-c-Met therapeutic antibody or an anti-c-Met chemotherapeutic agent to the patient for a time and under conditions that permit the antibody or the Fab fragment to bind to the ECD of mature human c-Met;

(b) optionally, removing any non-specifically bound antibody or Fab fragment; and (c) detecting and/or quantifying the amount of the antibody or Fab fragment of claim 1 which is specifically bound to the ECD, wherein a response to the administration of the anti-c-Met therapeutic antibody or the anti-c-Met chemotherapeutic agent to an individual is measured when the amount of the antibody or Fab fragment detected or quantified in (c) is greater in (i) as compared to (ii).

* * * * *